(12) United States Patent
Chatani et al.

(10) Patent No.: US 9,018,446 B2
(45) Date of Patent: Apr. 28, 2015

(54) GENES THAT INCREASE PLANT OIL AND METHOD FOR USING THE SAME

(71) Applicant: Toyota Jidosha Kabushiki Kaisha, Toyota-shi, Aichi-ken (JP)

(72) Inventors: Hiroshi Chatani, Toyota (JP); Chikara Ohto, Toyota (JP); Yukio Okamura, Toyota (JP); Norihiro Mitsukawa, Toyota (JP); Nobuhiko Muramoto, Aichi-gun (JP); Tomotsugu Koyama, Tsukuba (JP); Kyoko Matsui, Tsukuba (JP); Masaru Takagi, Tsukuba (JP)

(73) Assignee: Toyota Jidosha Kabushiki Kaisha, Aichi-ken (JP)

( * ) Notice: Subject to any disclaimer, the term of this patent is extended or adjusted under 35 U.S.C. 154(b) by 0 days.

(21) Appl. No.: 14/222,130

(22) Filed: Mar. 21, 2014

(65) Prior Publication Data

US 2014/0223601 A1 Aug. 7, 2014

Related U.S. Application Data

(62) Division of application No. 12/746,640, filed as application No. PCT/JP2008/072158 on Dec. 5, 2008.

(30) Foreign Application Priority Data

Dec. 5, 2007 (JP) ................. 2007-315272

(51) Int. Cl.
| | |
|---|---|
| *C12N 15/87* | (2006.01) |
| *C07H 21/04* | (2006.01) |
| *A01H 5/00* | (2006.01) |
| *C12N 5/10* | (2006.01) |
| *C12N 15/82* | (2006.01) |
| *A01H 5/02* | (2006.01) |
| *C07K 14/415* | (2006.01) |

(52) U.S. Cl.
CPC ........ *C12N 15/8247* (2013.01); *C07K 2319/80* (2013.01); *A01H 5/02* (2013.01); *C07K 14/415* (2013.01); *C12N 15/8216* (2013.01); *C12N 15/8217* (2013.01); *C12N 15/8261* (2013.01)

(58) Field of Classification Search
None
See application file for complete search history.

(56) References Cited

U.S. PATENT DOCUMENTS

| 5,516,668 | A |   | 5/1996 | Maruta |
| 5,783,394 | A | * | 7/1998 | Bestwick et al. ............ 435/6.12 |
| 5,914,449 | A |   | 6/1999 | Murase et al. |
| 6,717,034 | B2 |   | 4/2004 | Jiang |
| 7,342,148 | B2 |   | 3/2008 | Takagi et al. |
| 2003/0101481 | A1 |   | 5/2003 | Zhang et al. |
| 2003/0226173 | A1 |   | 12/2003 | Ratcliffe et al. |
| 2004/0006797 | A1 |   | 1/2004 | Shi et al. |
| 2004/0045049 | A1 |   | 3/2004 | Zhang et al. |
| 2004/0093638 | A1 |   | 5/2004 | Sasaki et al. |
| 2005/0005333 | A1 |   | 1/2005 | Ruezinsky et al. |
| 2005/0183169 | A1 | * | 8/2005 | Takagi et al. ................. 800/288 |
| 2006/0107345 | A1 |   | 5/2006 | Alexandrov et al. |
| 2006/0272060 | A1 |   | 11/2006 | Heard et al. |
| 2007/0022495 | A1 |   | 1/2007 | Reuber et al. |
| 2008/0072340 | A1 |   | 3/2008 | Troukhan et al. |
| 2008/0096277 | A1 |   | 4/2008 | Kuroda |
| 2009/0019605 | A1 |   | 1/2009 | Takagi et al. |
| 2009/0094717 | A1 |   | 4/2009 | Troukhan et al. |
| 2009/0116723 | A1 |   | 5/2009 | Okajima et al. |
| 2009/0178161 | A1 |   | 7/2009 | Arar et al. |
| 2009/0190821 | A1 |   | 7/2009 | Marugame |
| 2009/0300790 | A1 |   | 12/2009 | Aharoni et al. |
| 2011/0010804 | A1 |   | 1/2011 | Chatani et al. |
| 2011/0081691 | A1 |   | 4/2011 | Ohto et al. |
| 2011/0099664 | A1 |   | 4/2011 | Takagi et al. |
| 2011/0209244 | A1 |   | 8/2011 | Takagi et al. |

FOREIGN PATENT DOCUMENTS

| EP | 1469010 A1 | 10/2004 |
| EP | 1586652 A1 | 10/2005 |
| EP | 01702508 A1 | 9/2006 |
| JP | 60-2023 B2 | 1/1985 |
| JP | 02-035358 A | 2/1990 |
| JP | 06-090766 A | 4/1994 |
| JP | 6-217719 A | 8/1994 |
| JP | 6-303925 A | 11/1994 |
| JP | 9-182 A | 1/1997 |
| JP | 9-65840 A | 3/1997 |
| JP | 09-313059 A | 12/1997 |

(Continued)

OTHER PUBLICATIONS

White and Benning 2001 Plant Physiol. Biochemistry 39: p. 263-270.*
Shen et al 2006 Plant Molecular Biology 60: p. 377-387.*
V. R. Bautista, et al., "Arabidopsis ORF Clones", NEB1 Sequence Viewer V 2.0, GenBank Accession BT029518, GI: 119360090, 2006.
International Search Report for International Application No. PCT/JP2008/072158, dated Feb. 24, 2009.
Alex Cernac, et al., "Wrinkled1 encodes an AP2/EREB domain protein involved in the control of storage compound biosynthesis in *Arabidopsis*", The Plant Journal, 2004, pp. 575-585, vol. 40, Blackwell Publishing Ltd.

(Continued)

*Primary Examiner* — Eileen B O Hara
*Assistant Examiner* — Matthew Keogh
(74) *Attorney, Agent, or Firm* — Sughrue Mion, PLLC

(57) ABSTRACT

This invention is intended to be used to search for a transcription factor having novel functions of increasing the weight of an individual plant, increasing the weight of a given tissue per individual plant, or improving the productivity of a given substance per individual plant and to improve such properties in the plant. The weight of an individual plant is increased, the weight of a given tissue per individual plant is increased, the productivity of a given substance per individual plant is improved, or the content of a given substance per given tissue of a plant is increased via expression of a transcription factor that has been modified to suppress transcription accelerating activity.

5 Claims, 2 Drawing Sheets

(56) References Cited

FOREIGN PATENT DOCUMENTS

| | | |
|---|---|---|
| JP | 2001-059842 A | 3/2001 |
| JP | 3149951 B2 | 3/2001 |
| JP | 2001-269176 A | 10/2001 |
| JP | 2001-269177 A | 10/2001 |
| JP | 2001-269178 A | 10/2001 |
| JP | 2001-269179 A | 10/2001 |
| JP | 2001-292776 A | 10/2001 |
| JP | 2001-292777 A | 10/2001 |
| JP | 2001-333705 A | 12/2001 |
| JP | 3289043 B2 | 6/2002 |
| JP | 2002-524028 A | 8/2002 |
| JP | 3407033 B2 | 3/2003 |
| JP | 3407034 B2 | 5/2003 |
| JP | 3407035 B2 | 5/2003 |
| JP | 3407036 B2 | 5/2003 |
| JP | 3409079 B2 | 5/2003 |
| JP | 3421740 B2 | 6/2003 |
| JP | 2004-500823 A | 1/2004 |
| JP | 2004-286666 A | 10/2004 |
| JP | 2005-013214 A | 1/2005 |
| JP | 2005-027654 A | 2/2005 |
| JP | 2005-052114 A | 3/2005 |
| JP | 3656104 A | 6/2005 |
| JP | 2005-192483 A | 7/2005 |
| JP | 2005-204573 A | 8/2005 |
| JP | 2005-204657 A | 8/2005 |
| JP | 2005-278422 A | 10/2005 |
| JP | 2005-295878 A | 10/2005 |
| JP | 2005-295879 A | 10/2005 |
| JP | 2005-325136 A | 11/2005 |
| JP | 2005-352571 A | 12/2005 |
| JP | 2006-006248 A | 1/2006 |
| JP | 2006-020607 A | 1/2006 |
| JP | 2006-034218 A | 2/2006 |
| JP | 2006-042729 A | 2/2006 |
| JP | 2006-042730 A | 2/2006 |
| JP | 2006-055125 A | 3/2006 |
| JP | 2006-101827 A | 4/2006 |
| JP | 2006-134188 A | 5/2006 |
| JP | 2006-325588 A | 7/2006 |
| JP | 2006-280242 A | 10/2006 |
| JP | 3829200 B2 | 10/2006 |
| JP | 3995211 B2 | 10/2007 |
| JP | 2008-502358 A | 1/2008 |
| JP | 2009-009290 A | 1/2009 |
| JP | 2009-115598 A | 5/2009 |
| JP | 2009-180539 A | 8/2009 |
| JP | 2009-210409 A | 9/2009 |
| WO | 00/05385 A1 | 2/2000 |
| WO | 01/35727 A1 | 5/2001 |
| WO | 01/36597 A1 | 5/2001 |
| WO | 01/64022 A2 | 9/2001 |
| WO | 03/013227 A2 | 2/2003 |
| WO | 03/055903 A1 | 7/2003 |
| WO | 2004/046336 A2 | 6/2004 |
| WO | 2004/056993 A1 | 7/2004 |
| WO | 2005/047516 A2 | 5/2005 |
| WO | 2005/085467 A1 | 9/2005 |
| WO | 2006/056701 A1 | 6/2006 |
| WO | 2006/133461 A1 | 12/2006 |
| WO | 2007/102346 A1 | 9/2007 |
| WO | 2007/117693 A2 | 10/2007 |
| WO | 2008/041693 A1 | 4/2008 |
| WO | 2010/035618 A1 | 4/2010 |
| WO | 2010/041423 A1 | 4/2010 |

OTHER PUBLICATIONS

Anders M. Lindroth, et al., "Requirement of Chromomethylase3 for Maintenance of CpXpG Methylation", Science, Jun. 2001, pp. 2077-2080, vol. 292, American Association for the Advancement of Science, Washington, DC.

Colette Jako, et al., "Seed-Specific Over-Expression of an *Arabidopsis* cDNA Encoding a Diacylglycerol Acyltransferase Enhances Seed Oil Content and Seed Weight", Plant Physiology, Jun. 2001, pp. 861-874, vol. 126, American Society of Plant Physiologists.

Daniel Zilberman, et al., "Argonaute4 Control of Locus-Specific siRNA Accumulation and DNA and Histone Methylation", Science, Jan. 2003, pp. 716-719, vol. 299, American Association for the Advancement of Science.

J. Christopher Gaiser, et al., "The *Arabidopsis* Superman Gene Mediates Asymmetric Growth of the Outer Integument of Ovules", The Plant Cell, Mar. 1995, pp. 333-345, vol. 7, American Society of Plant Physiologists.

James P. Jackson, et al., "Control of CpNpG DNA methylation by the Kryptonite histone H3 methyltransferase", Letters to Nature, Apr. 2002, pp. 556-560, vol. 416, Macmillan Magazines Ltd.

John L. Bowman, et al., "Superman, a regulator of floral homeotic genes in *Arabidopsis*", Development, 1992, pp. 599-615, vol. 114, The Company of Biologists Limited, Great Britian.

Keiichiro Hiratsu, et al., "Dominant repression of target genes by chimeric repressors that include the EAR motif, a repression domain, in *Arabidopsis*", The Plant Journal, 2003, pp. 733-739, vol. 34, Blackwell Publishing Ltd.

Keiichiro Hiratsu, et al., "Identification of the minimal repression domain of Superman shows that the DLELRL hexapeptide is both necessary and sufficient for repression of transcription in *Arabidopsis*", Biochemical and Biophysical Research Communications, 2004, pp. 172-178, vol. 321, Elsevier Inc.

Keiichiro Hiratsu, et al., "The Superman protein is an active repressor whose carboxy-terminal repression domain is required for the development of normal flowers", Federation of European Biochemical Societies, 2002, pp. 351-354, vol. 514, Elsevier Science B.V.

Keith Roesler, et al., "Targeting of the *Arabidopsis* Homomeric Acetyl-Coenzyme A Carboxylase to Plastids of Rapeseeds", Plant Physiology, 1997, pp. 75-81, vol. 113, Clearance Center.

Koji Goto, et al., "Function and regulation of the *Arabidopsis* floral homeotic gene Pistillata", Genes & Development, 1994, pp. 1548-1560, vol. 8, Cold Spring Harbor Laboratory Press.

Kyoko Matsui, et al., "Suppression of the biosynthesis of proanthocyanidin in *Arabidopsis* by a chimeric PAP1 repressor", Plant Biotechnology Journal, 2004, pp. 487-493, vol. 2, Blackwell Publishing Ltd.

Kyoko Matsui, "A Chimeric AtMYB23 Repressor Induces Hairy Roots, Elongation of Leaves and Stems, and Inhibition of the Deposition of Mucilage on Seed Coats in *Arabidopsis*", Plant Cell Physiology, 2005, pp. 147-155, vol. 46(1).

Kyoko Matsui, et al., "Bio Medical Quick Review Net", 2004, pp. 1-6, vol. 4006.

Lu Tian et al., "Blocking histone deacetylation in *Arabidopsis* induces pleiotropic effects on plant gene regulation and development", PNAS, Jan. 2001, pp. 200-205, vol. 98, No. 1.

Masaru Ohta, et al., "Repression Domains of Class II ERF Transcriptional Repressors Share and Essential Motif for Active Repression", The Plant Cell, Aug. 2001, pp. 1959-1968, vol. 13, American Society of Plant Biologists.

Steven E. Jacobsen, et al., "Ectopic hypermethylation of flower-specific genes in *Arabidopsis*", Current Biology, 2000, pp. 179-186, vol. 10, No. 4, Elsevier Science Ltd.

Steven E. Jacobsen, et al., "Hypermethylated Superman Epigenetic Alleles in *Arabidopsis*", Science, Aug. 1997, pp. 1100-1103, vol. 277, American Association for the Advancement of Science, Washington, DC.

Toshitsugu Nakano, "Genome-Wide Analysis of the ERF Gene Family in *Arabidopsis* and Rice", Plant Physiology, Feb. 2006, pp. 411-432, vol. 140, American Society of Plant Biologists.

V. R. Bautista, et al., "*Arabidopsis* DRF Clones", NEB1 Sequence Viewer V 2.0, GenBank Accession BT029518, GI: 119360090, 2006.

Xiaofeng Cao, et al., "Locus-specific control of asymmetric and CpNpG methylation by to DRM and CMT3 methyltransferase genes", PNAS, Dec. 2002, pp. 16491-16498, vol. 99, Suppl. 4.

Xiaofeng Cao, et al., "Role of the *Arabidopsis* DRM Methyltransferases in De Novo DNA Methylation and Gene Silencing", Current Biology, Jul. 2002, pp. 1138-1144, vol. 12, Elsevier Science Ltd.

Y. Pan, et al., "Molecular Cloning, Expression, Phylogenetic and Functional Characterization of the *Arabidopsis* AP2/EREBP Tran-

(56) References Cited

OTHER PUBLICATIONS scription Factor Family", NCB1 Sequence Viewer V2.0 (Nucleotide), GenBank Accession AY560877, GI: 48479345, 2004.
Extended European Search Report (EESR) for corresponding European Patent Application No. 08 85 8128 dated Nov. 15, 2010.
Weselake R J et al: "Increasing the flow of carbon into seed oil", Biotechnology Advances, Elsevier Publishing, Barking, GB, LNKD-DOI:10.1016/J.BIOTECHADV.2009.07.001, vol. 27, No. 6, Nov. 1, 2009, pp. 866-878, XP026675573 ISSN: 0734-9750.
Zhang J Z: "Overexpression Analysis of Plant Transcription Factors", Current Opinion in Plant Biology, Quadrant Subscription Services, GB LNKD-DOI:10.1016/51369-5266(03)00081-5, vol. 6, No. 5, Oct. 1, 2003, pp. 430-440, XP 001180245 ISSN: 1369-5266.
Chen Yanhui et al: "The MYB Transcription Factor Superfamily of *Arabidopsis*: Expression Analysis and Phylogenetic Comparison with the Rice MYB Family", Plant Molecular Biology, Kluwer Academic Publishers, Dordrecht, NL LNKD-DOI:10.1007/511103-005-2910-Y, vol. 60, No. 1, Jan. 1, 2006, pp. 107-124, XP019262824 ISSN: 1573-5028.
Extended European Search Report (EESR) for corresponding European Patent Application No. 08 85 6425 dated Nov. 3, 2010.
Haiwei H. Guo et al., "Protein tolerance to random amino acid change", PNAS, 2004, 101(25): 9205-9210.
K. Diane Jofuku et al., "Control of seed mass and seed yield by the floral homeotic gene APETALA2", PNAS, 2005, 102(8): 3117-3122.
Nobutaka Mitsuda et al., "Comprehensive functional analysis of plant-specific NAC transcription factor family using the CRES-T method", Abstracts of the 45$_{th}$ Annual Meeting of the Japanese Society of Plant Physiologists, 2004, P4-B-16 (813).
Chikara Ohto et al., "Artificial Chimeric Repressors Can Increase Seed Oil Content and Plant Biomass", 22$_{nd}$ Internationals Conference on Arabidopsis Research, 2011, Publication: 501746623.
"Represent" from Merriam-Webster Dictionary, Retrieved from http://www.merriamwebster.com/dictionary/represents on Feb. 5, 2013.
Shinichiro Sawa, "Overexpression of the *AtmybL2* Gene Represses Trichome Development in *Arabidopsis*", DNA Research, 2002, 9: 31-34.
Ralf Stracke et al., "The *R2R3-MYB* gene family in *Arabidopsis thaliana*", Current Opinion in Plant Biology, 2001, 4: 447-456.
S. Takada et al., Genbank Accession No. AB049071, *Arabidopsis thaliana* AtNAC2 mRNA, 2006, 3 pages.
Geoffrey M. Wahl et al., "Molecular Hybridization of Immobilized Nucleic Acids: Theoretical Concepts and Practical Considerations", Methods in Enzymology, 1987, 152: 399-407.
K. Yamada et al., Genbank Accession No. BT005044, *Arabidopsis thaliana* clone U20756 putative jasmonic acid regulatory protein (At3g15510) mRNA, 2003, 3 pages.
Gaiyun Zhang et al., Phylogeny, gene structures, and expression patterns of the ERF gene family in soybean (*Glycine max* L.), Journal of Experimental Botany, 2008, 59(15): 4095-4107.
Restriction and Election of Species Requirement issued Aug. 16, 2012, in U.S. Appl. No. 12/746,577.
Non-Final Office Action issued Feb. 15, 2013, in U.S. Appl. No. 12/746,577.
Non-Final Office Action issued Feb. 19, 2013 in U.S. Appl. No. 12/921,060.
Mingjie Chen et al., "System Analysis of an *Arabidopsis* Mutant Altered in de Novo Fatty Acid Synthesis Reveals Diverse Changes in Seed Composition and Metabolism", Plant Physiology, 2009, 150: 27-41.
Antony N. Dodd et al., "Plant Circadian Clocks Increase Photosynthesis, Growth, Survival, and Competitive Advantage", Science, 2005, 309: 630-633.
John Doebley et al., "The evolution of apical dominance in maize", Nature, 1997, 386: 485-488.
Yongfeng Guo et al., "AtNAP, a NAC family transcription factor, has an important role in leaf senescence", The Plant Journal, 2006, 46: 601-612.

Yuxin Hu et al., "The *Arabidopsis* Auxin-Inducible Gene *Argos* Controls Lateral Organ Size", The Plant Cell, 2003, 15: 1951-1961.
Yuxin Hu. et al., "The *Arabidopsis Argos-Like* gene regulates cell expansion during organ growth", The Plant Journal, 2006, 47:1-9.
International Search Report for International Application No. PCT/JP2010/059543, dated Aug. 17, 2010.
Tomotsugu Koyama et al., "TCP Transcription Factors Control the Morphology of Shoot Lateral Organs via Negative Regulation of the Expression of Boundary-Specific Genes in *Arabidopsis*", The Plant Cell, 2007, 19: 473-484.
Minoru Kubo et al., "Transcription switches for protoxylem and metaxylem vessel formation", Genes & Development, 2005, 19: 1855-1860.
Norihito Kuno et al., "The Novel MYB Protein Early-Phytochrome-Responsive1 is a Component of a Slave Circadian Oscillator in *Arabidopsis*", The Plant Cell, 2003, 15: 2476-2488.
Makoto Kusaba et al., "Low glutelin content1: A Dominant Mutation that Suppresses the Glutelin Multigene Family via RNA Silencing in Rice", The Plant Cell, 2003, 15: 1455-1467.
Hon-Ming Lam, et al., "Overexpression of the *ASN1* Gene Enhances Nitrogen Status in Seeds of *Arabidopsis*", Plant Physiology, 2003, 132: 926-935.
Jisheng Li et al., "*Arabidopsis* H$^+$-PPase AVP1 Regulates Auxin-Mediated Organ Development", Science, 2005, 310: 121-125.
Yoshiyuki Maruta et al., "Transgenic rice with reduced glutelin content by transformation with glutelin A antisense gene", Molecular Breeding, 2001, 8:273-284.
Kyoko Matsui et al., "AtMYBL2, a protein with a single MYB domain, acts as a negative regulator of anthocyanin biosynthesis in *Arabidopsis*", The Plant Journal, 2008, 55: 954-967.
Akane Matsushita et al., "AGF1, an AT-Hook Protein, Is Necessary for the Negative Feedback of *AtGA3ox1* Encoding GA 3-Oxidase", Plant Physiology, 2007, 143: 1152-1162.
Nobutaka Mitsuda et al., "NAC Transcription Factors, NST1 and NST3, Are Key Regulators of the Formation of Secondary Walls in Woody Tissues of *Arabidopsis*", The Plant Cell, 2007, 19: 270-280.
Yukiko Mizukami et al., "Plant organ size control: *Aintegumenta* regulates growth and cell numbers during organogenesis", PNAS, 2000, 97(2): 942-947.
Nobuhiko Muramoto et al., "Identification of transcription factors responsible for seed oil content by Chimeric Repressor Gene-Silencing Technology (CRES-T)", Supplemental to Plant and Cell Physiology, 2008, 49: 152.
Zhongfu Ni et al., "Altered circadian rhythms regulate growth vigour in hybrids and allopolyploids", Nature, 2009, 457: 327-331.
Akio Ohyama et al., "Environmental risk evaluation of rice plants transformed with chimeric antisense cDNA for glutelin", Breeding Research, 2001, 3: 139-149.
Diego Mauricio Riaño-Pachón et al., "Pln TFDB an integrative plant transcription factor database", BMC Bioinformatics, 2007, 8(42): 1-10.
Monica Santos-Mendoza et al., "Deciphering gene regulatory networks that control seed development and maturation in *Arabidopsis*", The Plant Journal, 2008, 54: 608-620.
Marie C. Schruff et al., "The *Auxin Response Factor 2* gene of *Arabidopsis* links auxin signalling, cell division, and the size of seeds and other organs", Development, 2005, 133: 251-261.
Taito Takeda et al., "RNA interference of the *Arabidopsis* putative transcription factor TCP16 gene results in abortion of early pollen development", Plant Molecular Biology, 2006, 61: 165-177.
Office Action issued in U.S. Appl. No. 12/921,060, dated Oct. 8, 2013.
Office Action issued in U.S. Appl. No. 12/746,577, dated Oct. 23, 2013.
Bo Shen et al., "The homeobox gene *Glabra2* affects seed oil content in *Arabidopsis*", Plant Molecular Biology, 2006, 60: 377-387.
Joseph White et al., "Genomic approaches towards the engineering of oil seeds", Plant Physiol. Biochemistry, 2001, 39: 263-270.
Christian Dubos et al., "MYB transcription factors in *Arabidopsis*", Trends in Plant Science, 2010, 15(10): 573-581.

* cited by examiner

SEQUENCE LISTING

```
<160> NUMBER OF SEQ ID NOS: 17

<210> SEQ ID NO 1
<211> LENGTH: 999
<212> TYPE: DNA
<213> ORGANISM: Arabidopsis thaliana
<220> FEATURE:
<221> NAME/KEY: CDS
<222> LOCATION: (1)..(999)

<400> SEQUENCE: 1 atg gct gaa cga aag aaa cgc tct tct att caa acc aat aaa ccc aac      48
Met Ala Glu Arg Lys Lys Arg Ser Ser Ile Gln Thr Asn Lys Pro Asn
1               5                  10                  15 aaa aaa ccc atg aag aag aaa cct ttt cag cta aat cac ctc cca ggt      96
Lys Lys Pro Met Lys Lys Lys Pro Phe Gln Leu Asn His Leu Pro Gly
            20                  25                  30
```

| | | | | | | | | | | | | | | | | |
|---|---|---|---|---|---|---|---|---|---|---|---|---|---|---|---|---|
| tta | tct | gaa | gat | ttg | aag | act | atg | aga | aaa | ctc | cgt | ttc | gtt | gtg | aat | 144 |
| Leu | Ser | Glu | Asp | Leu | Lys | Thr | Met | Arg | Lys | Leu | Arg | Phe | Val | Val | Asn | |
| | | 35 | | | | 40 | | | | 45 | | | | | | |
| gat | cct | tac | gct | act | gac | tac | tca | tca | agc | gaa | gaa | gaa | gaa | agg | agt | 192 |
| Asp | Pro | Tyr | Ala | Thr | Asp | Tyr | Ser | Ser | Ser | Glu | Glu | Glu | Glu | Arg | Ser | |
| | 50 | | | | | 55 | | | | 60 | | | | | | |
| cag | aga | agg | aaa | cgt | tat | gtc | tgt | gag | atc | gat | ctt | cct | ttc | gct | caa | 240 |
| Gln | Arg | Arg | Lys | Arg | Tyr | Val | Cys | Glu | Ile | Asp | Leu | Pro | Phe | Ala | Gln | |
| 65 | | | | | 70 | | | | | 75 | | | | | 80 | |
| gct | gct | act | caa | gca | gaa | tct | gaa | agc | tca | tat | tgt | cag | gag | agt | aac | 288 |
| Ala | Ala | Thr | Gln | Ala | Glu | Ser | Glu | Ser | Ser | Tyr | Cys | Gln | Glu | Ser | Asn | |
| | | | | 85 | | | | 90 | | | | | 95 | | | |
| aat | aat | ggt | gta | agc | aag | act | aaa | atc | tca | gct | tgt | agc | aaa | aag | gtt | 336 |
| Asn | Asn | Gly | Val | Ser | Lys | Thr | Lys | Ile | Ser | Ala | Cys | Ser | Lys | Lys | Val | |
| | | | 100 | | | | | 105 | | | | 110 | | | | |
| tta | cgc | agc | aaa | gca | tct | ccg | gtc | gtt | gga | cgt | tct | tct | act | act | gtc | 384 |
| Leu | Arg | Ser | Lys | Ala | Ser | Pro | Val | Val | Gly | Arg | Ser | Ser | Thr | Thr | Val | |
| | | 115 | | | | | 120 | | | | | 125 | | | | |
| tcg | aag | cct | gtt | ggt | gtt | agg | cag | agg | aaa | tgg | ggt | aaa | tgg | gct | gct | 432 |
| Ser | Lys | Pro | Val | Gly | Val | Arg | Gln | Arg | Lys | Trp | Gly | Lys | Trp | Ala | Ala | |
| 130 | | | | | 135 | | | | | 140 | | | | | | |
| gag | att | aga | cat | cca | atc | acc | aaa | gta | aga | act | tgg | ttg | ggt | act | tac | 480 |
| Glu | Ile | Arg | His | Pro | Ile | Thr | Lys | Val | Arg | Thr | Trp | Leu | Gly | Thr | Tyr | |
| 145 | | | | | 150 | | | | | 155 | | | | | 160 | |
| gag | acg | ctt | gaa | caa | gca | gct | gat | gct | tat | gct | acc | aag | aag | ctt | gag | 528 |
| Glu | Thr | Leu | Glu | Gln | Ala | Ala | Asp | Ala | Tyr | Ala | Thr | Lys | Lys | Leu | Glu | |
| | | | | 165 | | | | 170 | | | | | 175 | | | |
| ttt | gat | gct | ctg | gct | gca | gcc | act | tct | gct | gct | tcc | tct | gtt | ttg | tca | 576 |
| Phe | Asp | Ala | Leu | Ala | Ala | Ala | Thr | Ser | Ala | Ala | Ser | Ser | Val | Leu | Ser | |
| | | | 180 | | | | | 185 | | | | | 190 | | | |
| aat | gag | tct | ggt | tct | atg | atc | tca | gcc | tca | ggg | tca | agc | att | gat | ctt | 624 |
| Asn | Glu | Ser | Gly | Ser | Met | Ile | Ser | Ala | Ser | Gly | Ser | Ser | Ile | Asp | Leu | |
| | | 195 | | | | | 200 | | | | | 205 | | | | |
| gac | aag | aag | cta | gtt | gat | tcg | act | ctt | gat | caa | caa | gct | ggt | gaa | tcg | 672 |
| Asp | Lys | Lys | Leu | Val | Asp | Ser | Thr | Leu | Asp | Gln | Gln | Ala | Gly | Glu | Ser | |
| 210 | | | | | 215 | | | | | 220 | | | | | | |
| aag | aaa | gcg | agt | ttt | gat | ttc | gac | ttt | gca | gat | cta | cag | att | cct | gaa | 720 |
| Lys | Lys | Ala | Ser | Phe | Asp | Phe | Asp | Phe | Ala | Asp | Leu | Gln | Ile | Pro | Glu | |
| 225 | | | | | 230 | | | | | 235 | | | | | 240 | |
| atg | ggt | tgc | ttc | att | gat | gac | tca | ttc | atc | cca | aat | gct | tgt | gag | ctt | 768 |
| Met | Gly | Cys | Phe | Ile | Asp | Asp | Ser | Phe | Ile | Pro | Asn | Ala | Cys | Glu | Leu | |
| | | | | 245 | | | | | 250 | | | | | 255 | | |
| gat | ttt | ctc | tta | aca | gaa | gag | aac | aac | aac | caa | atg | ttg | gat | gat | tac | 816 |
| Asp | Phe | Leu | Leu | Thr | Glu | Glu | Asn | Asn | Asn | Gln | Met | Leu | Asp | Asp | Tyr | |
| | | | 260 | | | | | 265 | | | | | 270 | | | |
| tgt | ggc | ata | gat | gat | ctg | gac | atc | att | ggt | ctt | gaa | tgt | gac | ggt | cca | 864 |
| Cys | Gly | Ile | Asp | Asp | Leu | Asp | Ile | Ile | Gly | Leu | Glu | Cys | Asp | Gly | Pro | |
| | | 275 | | | | | 280 | | | | | 285 | | | | |
| agc | gaa | ctt | cca | gac | tat | gat | ttc | tca | gat | gtg | gag | atc | gat | ctt | ggt | 912 |
| Ser | Glu | Leu | Pro | Asp | Tyr | Asp | Phe | Ser | Asp | Val | Glu | Ile | Asp | Leu | Gly | |
| | 290 | | | | | 295 | | | | | 300 | | | | | |
| ctc | att | gga | acc | acc | att | gac | aag | tat | gct | ttc | gtt | gat | cat | atc | gca | 960 |
| Leu | Ile | Gly | Thr | Thr | Ile | Asp | Lys | Tyr | Ala | Phe | Val | Asp | His | Ile | Ala | |
| 305 | | | | | 310 | | | | | 315 | | | | | 320 | |
| aca | act | act | ccc | act | cct | ctt | aat | atc | gcg | tgc | cca | taa | | | | 999 |
| Thr | Thr | Thr | Pro | Thr | Pro | Leu | Asn | Ile | Ala | Cys | Pro | | | | | |
| | | | | 325 | | | | | 330 | | | | | | | |

<210> SEQ ID NO 2
<211> LENGTH: 332

<212> TYPE: PRT
<213> ORGANISM: Arabidopsis thaliana

<400> SEQUENCE: 2

```
Met Ala Glu Arg Lys Lys Arg Ser Ser Ile Gln Thr Asn Lys Pro Asn
1               5                   10                  15

Lys Lys Pro Met Lys Lys Pro Phe Gln Leu Asn His Leu Pro Gly
            20                  25                  30

Leu Ser Glu Asp Leu Lys Thr Met Arg Lys Leu Arg Phe Val Val Asn
        35                  40                  45

Asp Pro Tyr Ala Thr Asp Tyr Ser Ser Glu Glu Glu Arg Ser
        50                  55                  60

Gln Arg Arg Lys Arg Tyr Val Cys Glu Ile Asp Leu Pro Phe Ala Gln
65                  70                  75                  80

Ala Ala Thr Gln Ala Glu Ser Glu Ser Tyr Cys Gln Glu Ser Asn
            85                  90                  95

Asn Asn Gly Val Ser Lys Thr Lys Ile Ser Ala Cys Ser Lys Lys Val
            100                 105                 110

Leu Arg Ser Lys Ala Ser Pro Val Val Gly Arg Ser Thr Thr Val
        115                 120                 125

Ser Lys Pro Val Gly Val Arg Gln Arg Lys Trp Gly Lys Trp Ala Ala
130                 135                 140

Glu Ile Arg His Pro Ile Thr Lys Val Arg Thr Trp Leu Gly Thr Tyr
145                 150                 155                 160

Glu Thr Leu Glu Gln Ala Ala Asp Ala Tyr Ala Thr Lys Lys Leu Glu
            165                 170                 175

Phe Asp Ala Leu Ala Ala Ala Thr Ser Ala Ala Ser Ser Val Leu Ser
            180                 185                 190

Asn Glu Ser Gly Ser Met Ile Ser Ala Ser Gly Ser Ser Ile Asp Leu
        195                 200                 205

Asp Lys Lys Leu Val Asp Ser Thr Leu Asp Gln Gln Ala Gly Glu Ser
210                 215                 220

Lys Lys Ala Ser Phe Asp Phe Asp Phe Ala Asp Leu Gln Ile Pro Glu
225                 230                 235                 240

Met Gly Cys Phe Ile Asp Asp Ser Phe Ile Pro Asn Ala Cys Glu Leu
            245                 250                 255

Asp Phe Leu Leu Thr Glu Glu Asn Asn Asn Gln Met Leu Asp Asp Tyr
            260                 265                 270

Cys Gly Ile Asp Asp Leu Asp Ile Ile Gly Leu Glu Cys Asp Gly Pro
        275                 280                 285

Ser Glu Leu Pro Asp Tyr Asp Phe Ser Asp Val Glu Ile Asp Leu Gly
        290                 295                 300

Leu Ile Gly Thr Thr Ile Asp Lys Tyr Ala Phe Val Asp His Ile Ala
305                 310                 315                 320

Thr Thr Thr Pro Thr Pro Leu Asn Ile Ala Cys Pro
            325                 330
```

<210> SEQ ID NO 3
<211> LENGTH: 747
<212> TYPE: DNA
<213> ORGANISM: Arabidopsis thaliana
<220> FEATURE:
<221> NAME/KEY: CDS
<222> LOCATION: (1)..(747)

<400> SEQUENCE: 3

| | | |
|---|---|---|
| atg gag ggt tcg tcc aaa ggg ctg cga aaa ggt gct tgg act act gaa<br>Met Glu Gly Ser Ser Lys Gly Leu Arg Lys Gly Ala Trp Thr Thr Glu<br>1                      5                      10                  15 | | 48 |
| gaa gat agt ctc ttg aga cag tgc att aat aag tat gga gaa ggc aaa<br>Glu Asp Ser Leu Leu Arg Gln Cys Ile Asn Lys Tyr Gly Glu Gly Lys<br>                  20                      25                      30 | | 96 |
| tgg cac caa gtt cct gta aga gct ggg cta aac cgg tgc agg aaa agt<br>Trp His Gln Val Pro Val Arg Ala Gly Leu Asn Arg Cys Arg Lys Ser<br>                  35                      40                      45 | | 144 |
| tgt aga tta aga tgg ttg aac tat ttg aag cca agt atc aag aga gga<br>Cys Arg Leu Arg Trp Leu Asn Tyr Leu Lys Pro Ser Ile Lys Arg Gly<br>50                      55                      60 | | 192 |
| aaa ctt agc tct gat gaa gtc gat ctt ctt cgc ctt cat agg ctt<br>Lys Leu Ser Ser Asp Glu Val Asp Leu Leu Arg Leu His Arg Leu<br>65                      70                      75                      80 | | 240 |
| cta ggg aat agg tgg tct tta att gct gga aga tta cct ggt cgg acc<br>Leu Gly Asn Arg Trp Ser Leu Ile Ala Gly Arg Leu Pro Gly Arg Thr<br>                  85                      90                      95 | | 288 |
| gca aat gac gtc aag aat tac tgg aac act cat ctg agt aag aaa cat<br>Ala Asn Asp Val Lys Asn Tyr Trp Asn Thr His Leu Ser Lys Lys His<br>                100                      105                     110 | | 336 |
| gaa ccg tgt tgt aag ata aag atg aaa aag aga gac att acg ccc att<br>Glu Pro Cys Cys Lys Ile Lys Met Lys Lys Arg Asp Ile Thr Pro Ile<br>                115                      120                   125 | | 384 |
| cct aca aca ccg gca cta aaa aac aat gtt tat aag cct cga cct cga<br>Pro Thr Thr Pro Ala Leu Lys Asn Asn Val Tyr Lys Pro Arg Pro Arg<br>130                     135                      140 | | 432 |
| tcc ttc aca gtt aac aac gac tgc aac cat ctc aat gcc cca cca aaa<br>Ser Phe Thr Val Asn Asn Asp Cys Asn His Leu Asn Ala Pro Pro Lys<br>145                     150                      155                   160 | | 480 |
| gtt gac gtt aat cct cca tgc ctt gga ctt aac atc aat aat gtt tgt<br>Val Asp Val Asn Pro Pro Cys Leu Gly Leu Asn Ile Asn Asn Val Cys<br>                      165                      170                   175 | | 528 |
| gac aat agt atc ata tac aac aaa gat aag aag aaa gac caa cta gtg<br>Asp Asn Ser Ile Ile Tyr Asn Lys Asp Lys Lys Lys Asp Gln Leu Val<br>                  180                      185                   190 | | 576 |
| aat aat ttg att gat gga gat aat atg tgg tta gag aaa ttc cta gag<br>Asn Asn Leu Ile Asp Gly Asp Asn Met Trp Leu Glu Lys Phe Leu Glu<br>                195                     200                   205 | | 624 |
| gaa agc caa gag gta gat att ttg gtt cct gaa gcg acg aca aca gaa<br>Glu Ser Gln Glu Val Asp Ile Leu Val Pro Glu Ala Thr Thr Thr Glu<br>210                     215                      220 | | 672 |
| aag ggg gac acc ttg gct ttt gac gtt gat caa ctt tgg agt ctt ttc<br>Lys Gly Asp Thr Leu Ala Phe Asp Val Asp Gln Leu Trp Ser Leu Phe<br>225                     230                      235                   240 | | 720 |
| gat gga gag act gtg aaa ttt gat tag<br>Asp Gly Glu Thr Val Lys Phe Asp<br>                  245 | | 747 |

<210> SEQ ID NO 4
<211> LENGTH: 248
<212> TYPE: PRT
<213> ORGANISM: Arabidopsis thaliana

<400> SEQUENCE: 4

Met Glu Gly Ser Ser Lys Gly Leu Arg Lys Gly Ala Trp Thr Thr Glu
1                      5                      10                  15

Glu Asp Ser Leu Leu Arg Gln Cys Ile Asn Lys Tyr Gly Glu Gly Lys
                  20                      25                      30

Trp His Gln Val Pro Val Arg Ala Gly Leu Asn Arg Cys Arg Lys Ser

```
                35                  40                  45
Cys Arg Leu Arg Trp Leu Asn Tyr Leu Lys Pro Ser Ile Lys Arg Gly
 50                  55                  60

Lys Leu Ser Ser Asp Glu Val Asp Leu Leu Arg Leu His Arg Leu
 65                  70                  75                  80

Leu Gly Asn Arg Trp Ser Leu Ile Ala Gly Arg Leu Pro Gly Arg Thr
                 85                  90                  95

Ala Asn Asp Val Lys Asn Tyr Trp Asn Thr His Leu Ser Lys Lys His
            100                 105                 110

Glu Pro Cys Cys Lys Ile Lys Met Lys Lys Arg Asp Ile Thr Pro Ile
        115                 120                 125

Pro Thr Thr Pro Ala Leu Lys Asn Asn Val Tyr Lys Pro Arg Pro Arg
    130                 135                 140

Ser Phe Thr Val Asn Asn Asp Cys Asn His Leu Asn Ala Pro Pro Lys
145                 150                 155                 160

Val Asp Val Asn Pro Pro Cys Leu Gly Leu Asn Ile Asn Asn Val Cys
                165                 170                 175

Asp Asn Ser Ile Ile Tyr Asn Lys Asp Lys Lys Asp Gln Leu Val
            180                 185                 190

Asn Asn Leu Ile Asp Gly Asp Asn Met Trp Leu Glu Lys Phe Leu Glu
        195                 200                 205

Glu Ser Gln Glu Val Asp Ile Leu Val Pro Glu Ala Thr Thr Thr Glu
    210                 215                 220

Lys Gly Asp Thr Leu Ala Phe Asp Val Asp Gln Leu Trp Ser Leu Phe
225                 230                 235                 240

Asp Gly Glu Thr Val Lys Phe Asp
                245

<210> SEQ ID NO 5
<211> LENGTH: 21
<212> TYPE: DNA
<213> ORGANISM: Artificial Sequence
<220> FEATURE:
<223> OTHER INFORMATION: Synthetic DNA for a forward primer of At3g25890

<400> SEQUENCE: 5
atggctgaac gaaagaaacg c                                              21

<210> SEQ ID NO 6
<211> LENGTH: 21
<212> TYPE: DNA
<213> ORGANISM: Artificial Sequence
<220> FEATURE:
<223> OTHER INFORMATION: Synthetic DNA for a reverse primer of At3g25890

<400> SEQUENCE: 6
tgggcacgcg atattaagag g                                              21

<210> SEQ ID NO 7
<211> LENGTH: 23
<212> TYPE: DNA
<213> ORGANISM: Artificial Sequence
<220> FEATURE:
<223> OTHER INFORMATION: Synthetic DNA for a forward primer of At1g56650

<400> SEQUENCE: 7
gatggagggt tcgtccaaag ggc                                            23

<210> SEQ ID NO 8
```

```
<211> LENGTH: 25
<212> TYPE: DNA
<213> ORGANISM: Artificial Sequence
<220> FEATURE:
<223> OTHER INFORMATION: Synthetic DNA for a reverse primer of At1g56650

<400> SEQUENCE: 8
atcaaatttc acagtctctc catcg                                           25

<210> SEQ ID NO 9
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(10)
<223> OTHER INFORMATION: Xaa is any amino acid
<220> FEATURE:
<221> NAME/KEY: misc_feature
<222> LOCATION: (14)..(14)
<223> OTHER INFORMATION: Xaa is Asn or Glu
<220> FEATURE:
<221> NAME/KEY: misc_feature
<222> LOCATION: (16)..(21)
<223> OTHER INFORMATION: Xaa is any amino acid

<400> SEQUENCE: 9

Xaa Xaa Xaa Xaa Xaa Xaa Xaa Xaa Xaa Xaa Leu Asp Leu Xaa Leu Xaa
1               5                   10                  15

Xaa Xaa Xaa Xaa Xaa
            20

<210> SEQ ID NO 10
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(10)
<223> OTHER INFORMATION: Xaa is any amino acid
<220> FEATURE:
<221> NAME/KEY: misc_feature
<222> LOCATION: (15)..(15)
<223> OTHER INFORMATION: Xaa is Phe or Ile
<220> FEATURE:
<221> NAME/KEY: misc_feature
<222> LOCATION: (16)..(21)
<223> OTHER INFORMATION: Xaa is any amino acid

<400> SEQUENCE: 10

Xaa Xaa Xaa Xaa Xaa Xaa Xaa Xaa Xaa Xaa Phe Asp Leu Asn Xaa Xaa
1               5                   10                  15

Xaa Xaa Xaa Xaa Xaa
            20

<210> SEQ ID NO 11
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (6)..(6)
<223> OTHER INFORMATION: Xaa is Glu, Gln or Asp
<220> FEATURE:
<221> NAME/KEY: misc_feature
```

```
<222> LOCATION: (10)..(19)
<223> OTHER INFORMATION: Xaa is any amino acid

<400> SEQUENCE: 11

Leu Asp Leu Asp Leu Xaa Leu Arg Leu Xaa Xaa Xaa Xaa Xaa Xaa Xaa
1               5                   10                  15

Xaa Xaa Xaa

<210> SEQ ID NO 12
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa represents Glu, Gln, or Asp

<400> SEQUENCE: 12

Asp Leu Xaa Leu Arg Leu
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa represents Asp, Asn, Glu, Gln, Thr, or Ser
<220> FEATURE:
<221> NAME/KEY: misc_feature
<222> LOCATION: (3)..(3)
<223> OTHER INFORMATION: Xaa represents Asp, Gln, Asn, Arg, Glu, Thr,
      Ser, or His
<220> FEATURE:
<221> NAME/KEY: misc_feature
<222> LOCATION: (5)..(5)
<223> OTHER INFORMATION: Xaa represents Arg, Gln, Asn, Thr, Ser, His,
      Lys, or Asp

<400> SEQUENCE: 13

Xaa Leu Xaa Leu Xaa Leu
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa represents Asp, Asn, Glu, Gln, Thr, or Ser
<220> FEATURE:
<221> NAME/KEY: misc_feature
<222> LOCATION: (3)..(3)
<223> OTHER INFORMATION: Xaa represents Asp, Gln, Asn, Arg, Glu, Thr,
      Ser, or His
<220> FEATURE:
<221> NAME/KEY: misc_feature
<222> LOCATION: (5)..(5)
<223> OTHER INFORMATION: Xaa represents Gln, Asn, Thr, Ser, His, Lys, or
      Asp

<400> SEQUENCE: 14

Xaa Leu Xaa Leu Xaa Leu
```

```
<210> SEQ ID NO 15
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa represents Asp, Asn, Glu, Gln, Thr, or Ser
<220> FEATURE:
<221> NAME/KEY: misc_feature
<222> LOCATION: (3)..(3)
<223> OTHER INFORMATION: Xaa represents Asn, Arg, Thr, Ser, or His

<400> SEQUENCE: 15

Xaa Leu Xaa Leu Arg Leu
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa represents Asn, Glu, Gln, Thr, or Ser
<220> FEATURE:
<221> NAME/KEY: misc_feature
<222> LOCATION: (3)..(3)
<223> OTHER INFORMATION: Xaa represents Asp, Gln, Asn, Arg, Glu, Thr,
      Ser, or His

<400> SEQUENCE: 16

Xaa Leu Xaa Leu Arg Leu
1               5

<210> SEQ ID NO 17
<211> LENGTH: 13
<212> TYPE: PRT
<213> ORGANISM: Artificial Sequence
<220> FEATURE:
<223> OTHER INFORMATION: Synthetic peptide

<400> SEQUENCE: 17

Gly Leu Asp Leu Asp Leu Glu Leu Arg Leu Gly Phe Ala
1               5                   10
```

US 9,018,446 B2

GENES THAT INCREASE PLANT OIL AND METHOD FOR USING THE SAME

This is a Divisional Application of U.S. application Ser. No. 12/746,640 filed Jun. 7, 2010, which is a National Phase Application of PCT International Application No. PCT/JP2008/072158 filed on Dec. 5, 2008, which claims priority from Japanese Application No. 2007-315272 filed on Dec. 5, 2007. The entire disclosures of the prior applications are incorporated herein by reference.

BACKGROUND ART

The term "biomass" generally refers to the total amount of organisms that inhabit or exist in a given area. When such term is used for plants, in particular, the term refers to dry weight per unit area. A biomass unit is quantified in terms of a mass or an energy amount. In the case of plant biomass, the term "standing crop" is occasionally used to represent "biomass." Since plant biomass is generated by fixing atmospheric carbon dioxide with the use of the solar energy, it can be regarded as so-called "carbon-neutral energy." Accordingly, an increase plant biomass is effective for global environmental preservation, the prevention of global warming, and mitigation of greenhouse gas emissions. Thus, technologies for increasing the production of plant biomass have been industrially significant.

Plants are cultivated for the purpose of using some tissues thereof (e.g., seeds, roots, leaves, or stems) or for the purpose of producing various materials, such as a fat and oil. Examples of fat and oil produced from plants that have been heretofore known include soybean oil, sesame oil, olive oil, coconut oil, rice oil, cottonseed oil, sunflower oil, corn oil, safflower oil, and rapeseed oil. Such fat and oil are extensively used for household and industrial applications. Also, a fat and oil produced from plants is used as biodiesel fuels, and the applicability thereof is increasing for alternative energy to petroleum.

Under such circumstances, it is necessary for the industrial success of the production of the fat and oil using plants that the productivity per unit of cultivation area be improved. If the number of cultivated plants is assumed to be constant per unit of cultivation area, an improvement in the amount of fat and oil production per plant is found to be necessary. When fat and oil are extracted from seeds obtained from plants, an improvement in the amount of fat and oil production per plant can be achieved via techniques of, for example, improving the seed yield per plant or increasing the fat and oil content in seeds.

Techniques for increasing the amount of fat and oil production from plant seeds are roughly classified into techniques based on an improvement in cultivation methods and techniques based on the development of plant varieties that can increase the amount of fat and oil production. Techniques based on the development of plant varieties are roughly classified as conventional breeding techniques such as crossing and molecular breeding techniques via genetic recombination. As techniques for increasing the amount of fat and oil production via genetic recombination, A) a method of modifying synthetic pathways for triacylglycerol (TAG) of seeds, which is a main component of plant fat and oil, and B) a method of modifying regulatory genes that regulate plant morphogenesis or metabolism are known.

In the method A) above, the amount of TAGs synthesized from sugars produced via photosynthesis can be increased by (1) enhancing synthesis activities of fatty acids (i.e., TAG components) or a glycerol from sugars or (2) reinforcing the reaction of synthesizing TAGs from glycerol and fatty acids. In this regard, the following techniques have been reported as techniques using genetically engineering techniques. An example of (1) is a technique in which cytosolic Acetylcoenzyme A carboxylase (ACCase) of *Arabidopsis thaliana* is overexpressed in plastids of *Brassica rapa* L. ver. *Nippo-oleifera* and the fat and oil content in seeds is improved by 5% (Plant Physiology, 1997, Vol. 113, pp. 75-81).

An example of (2) is a technique of increasing the fat and oil production via overexpression of diacylglycerol acyltransferase (DGAT) that transfers an acyl group to the sn-3 position of diacylglycerol (Plant Physiology, 2001, Vol. 126, pp. 861-874). It is reported that the fat and oil content and the seed weight are increased as the DGAT expression level increases, and the number of seeds per plant may be occasionally increased according to the method of Plant Physiology, 2001, Vol. 126, pp. 861-874. The fat and oil content in *Arabidopsis thaliana* seeds was increased by 46% and the fat and oil amount per plant was increased by a maximum of about 125% by such technique.

As the method of B), expression of transcriptional factor genes associated with regulation of biosynthetic enzyme genes expression may be regulated. An example thereof is WO 01/35727. WO 01/35727 employs a technique in which recombinant plants are prepared via exhaustive overexpression or knocking out of transcriptional factors and genes that enhance the fat and oil content in seeds are then selected. WO 01/35727 discloses that overexpression of ERF subfamily B-4 transcriptional factor genes results in a 23% increase in the fat and oil content in seeds. WO 01/35727, however, does not disclose an increase or decrease in fat and oil content per plant. Also, Plant J., 2004, 40, 575-585 discloses the overexpression of WRINKLED1, which is a transcriptional factor having the AP2/EREB domain, improves the fat and oil content in seeds.

Although molecular breeding techniques as described above intended for the improvement of various traits have been developed, techniques for improving the yield involving increasing the weight of plant, increasing a given tissue, or improving the productivity of target substances have not yet been put to practical use.

Further, targets of techniques for increasing the production of target substances (fat and oil, in particular) via genetic recombination are dicotyledonous plants such as *Arabidopsis thaliana* and *Brassica rapa* L. ver. *Nippo-oleifera*. Techniques targeting monocotyledonous plants, such as rice and maize, are not yet known.

This is considered to be due to the following reasons. That is, truly excellent genes have not yet been discovered and new recombinant varieties that are found effective at the test phase cannot exhibit effects as expected during the practical phase under a variety of natural environments. In order to overcome such problems, the discovery of dramatically effective new genes and the development of genes exhibiting effects under practical environments, even if the effectiveness thereof is equivalent to that of existing genes, are necessary.

DISCLOSURE OF THE INVENTION

Object to be Attained by the Invention

Under given circumstances, the present invention is intended to be used to search for a transcription factor having new functions of increasing the weight of an individual plant, increasing the weight of a given tissue per individual plant, improving the productivity of a given substance per individual plant, or increasing the content of a given substance in a given tissue of a plant and to provide a technique that is capable of improving such features in a plant.

Means for Attaining the Object

The present inventors have conducted concentrated studies in order to attain the above object. As a result, they discovered that expression of a transcription factor that is modified so as to suppress transcription accelerating activity would lead to an increase in the weight of an individual plant, an increase in the weight of a given tissue per individual plant, an improvement in the productivity of a given substance per individual plant, or an increase in the content of a given substance in a given tissue of a plant. This has led to the completion of the present invention.

The plant according to the present invention attained increased individual plant weight, increased weight of a given tissue per individual plant, improved productivity of a given substance per individual plant, or increased content of a given substance in a given tissue of a plant via expression of a transcription factor with suppressed transcription accelerating activity.

In the present invention, transcription factor that belongs to the transcription factor family including a transcription factor comprising the amino acid sequence as shown in SEQ ID NO: 2, a transcription factor comprising the amino acid sequence as shown in SEQ ID NO: 4 can be used as the above-mentioned transcription factor.

The transcription factor is preferably any of proteins (a) to (c) below:

(a) a protein comprising the amino acid sequence as shown in SEQ ID NO: 2 or 4;

(b) a protein comprising an amino acid sequence derived from the amino acid sequence as shown in SEQ ID NO: 2 or 4 by deletion, substitution, addition, or insertion of 1 or a plurality of amino acids and having transcription accelerating activity; or (c) a protein encoded by a polynucleotide hybridizing under stringent conditions to a polynucleotide comprising a nucleotide sequence complementary to the nucleotide sequence as shown in SEQ ID NO: 1 or 3 and having transcription accelerating activity.

In particular, the plant according to the present invention can have suppressed transcription accelerating activity of a target transcription factor by expressing a chimeric protein resulting from the fusion of the target transcription factor with a functional peptide that converts an arbitrary transcription factor into a transcription repressor in a plant. Examples of the functional peptides include peptides represented by formulae (1) to (8) below:

(1) X1-Leu-Asp-Leu-X2-Leu-X3 (SEQ ID NO: 9 with deletion of 0-10 residues from the N-terminus)
wherein X1 represents 0 to 10 amino acid residues; X2 represents Asn or Glu; and X3 represents at least 6 amino acid residues;

(2) Y1-Phe-Asp-Leu-Asn-Y2-Y3 (SEQ ID NO: 10 with deletion of 0-10 residues from the N-terminus)
wherein Y1 represents 0 to 10 amino acid residues; Y2 represents Phe or Ile; and Y3 represents at least 6 amino acid residues;

(3) Z1-Asp-Leu-Z2-Leu-Arg-Leu-Z3 (SEQ ID NO: 11 with deletion of 0-10 residues from the C-terminus and deletion of 0-2 residues from the N-terminus)
wherein Z1 represents Leu, Asp-Leu, or Leu-Asp-Leu; Z2 represents Glu, Gln, or Asp; and Z3 represents 0 to 10 amino acid residues;

(4) Asp-Leu-Z4-Leu-Arg-Leu (SEQ ID NO: 12)
wherein Z4 represents Glu, Gln, or Asp;

(5) α1-Leu-β1-Leu-γ1-Leu (SEQ ID NO:13);
(6) α1-Leu-β1-Leu-γ2-Leu (SEQ ID NO:14);
(7) α1-Leu-β2-Leu-Arg-Leu (SEQ ID NO: 15); and
(8) α2-Leu-β1-Leu-Arg-Leu (SEQ ID NO: 16);

wherein, in formulae (5) to (8), α1 represents Asp, Asn, Glu, Gln, Thr, or Ser; α2 represents Asn, Glu, Gln, Thr, or Ser; β1 represents Asp, Gln, Asn, Arg, Glu, Thr, Ser, or His; β2 represents Asn, Arg, Thr, Ser, or His; γ1 represents Arg, Gln, Asn, Thr, Ser, His, Lys, or Asp; and γ2 represents Gln, Asn, Thr, Ser, His, Lys, or Asp.

In the plant according to the present invention, the seed weight as the weight of a given tissue can be improved. Also, in the plant according to the present invention, the productivity of a fat and oil as the productivity of a given substance described above can be improved.

The present invention can provide a method for producing a plant exhibiting increased individual plant weight, increased weight of a given tissue per individual plant, improved productivity of a given substance per individual plant, or increased content of a given substance in a given tissue of a plant via expression of a transcription factor with suppressed transcription accelerating activity.

Further, the present invention can provide a chimeric protein resulting from the fusion of a target transcription factor with a functional peptide that converts an arbitrary transcription factor into a transcription repressor, which is capable of increasing the weight of an individual plant, increasing the weight of a given tissue per individual plant, improving the productivity of a given substance per individual plant, or increasing the content of a given substance in a given tissue of a plant via suppression of transcription accelerating activity of the transcription factor; a polynucleotide encoding the chimeric protein; a recombinant expression vector containing the polynucleotide and a promoter; and a kit for improving properties of a plant in terms of the weight of a plant, the weight of a given tissue, the productivity of a given substance, or the content of a substance comprising the expression vector.

Effects of the Invention

The plant according to the present invention exhibits increased individual plant weight, increased weight of a given tissue per individual plant, improved productivity of a given substance per individual plant, or increased content of a given substance in a given tissue of a plant, compared with a wild-type plant. With the use of the plant according to the present invention, accordingly, the amount of production of the target biomass can be increased, the yield of the target tissue can be increased, the productivity of the target substance can be improved, and the content of the target substance in the target tissue can be increased. This enables production of biomass, plant tissue, or target substances at low cost.

Also, the chimeric protein according to the present invention can impart a plant with traits such as increased individual plant weight, increased weight of a given tissue per individual plant, improved productivity of a given substance per individual plant, or increased content of a given substance in a given tissue of a plant, compared with a wild-type plant. With the use of the chimeric protein according to the present invention, accordingly, a plant that can realize an increased amount of biomass production, increased yield of the target tissue, improved productivity of a target substance, or increased content of a target substance in the target tissue can be produced.

This description includes part or all of the contents as disclosed in the description and/or drawings of Japanese Patent Application No. 2007-315272, which is a priority document of the present application.

BEST MODES FOR CARRYING OUT THE INVENTION

Figure 1:
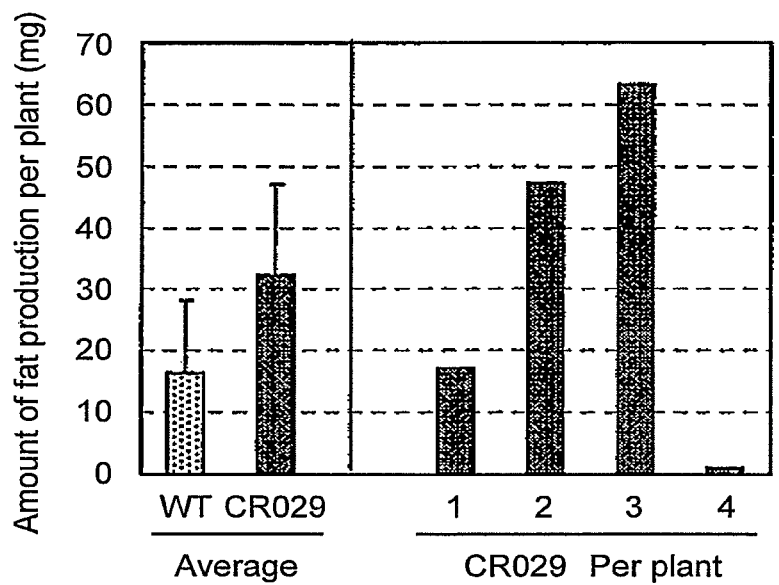
FIG. 1 is a characteristic diagram showing the results of measuring the amount of fat and oil production per individual plant in the T2 plant-T3 seeds (CR029) of a plant into which the transcription factor (At3g25890) with suppressed expression accelerating activity has been introduced.

Hereafter, the present invention is described in detail.

The plant according to the present invention exhibits increased individual plant weight, increased weight of a given tissue per individual plant, improved productivity of a given substance per individual plant, or increased content of a given substance in a given tissue, compared with a wild-type plant, via expression of a transcription factor with suppressed transcription accelerating activity. Specifically, the plant according to the present invention was produced by expressing a transcription factor with suppressed transcription accelerating activity in a plant of interest, so as to significantly improve the weight of a plant, the weight of a given tissue, the productivity of a given substance, or the content of a given substance therein.

The term "the increased weight of a plant" used herein refers to an increase in production of so-called biomass, i.e., an increase in the amount of biomass per given area. The amount of biomass produced per given area can be increased by increasing the planting density (i.e., the number of individual plants per given area) and by increasing the weight or energy amount per individual plant. Specifically, plant biomass can be evaluated in terms of dry weight per individual plant, as well as in terms of dry weight per given area.

In the present invention, accordingly, biomass may be defined in terms of the plant dry weight per individual plant, the dry weight of aerial parts per individual plant, the weight of a given tissue accumulating the target product per individual plant, the target product per individual plant, or the content of the target substance per given tissue.

The term "the weight of a given tissue per individual plant" used herein refers to the weight of at least 1 tissue selected from among tissues such as seeds, roots, leaves, stems, flowers, and pollen that constitute plants. Particularly preferably, the plant according to the present invention is intended to increase seed weight.

The term "the productivity of a given substance per individual plant" used herein refers to the contents of various substances generated by plants per individual plant. Substances are not particularly limited and may be naturally produced by plants. Alternatively, such substances may be not naturally produced by plants, but rather may be produced from plants via genetic engineering or other means. If the content of the target product per tissue is increased, in particular, purification and transportation costs can be reduced, and the industrial usefulness of such plants is significant. Specifically, target products may be lignocelluloses that account for substantially the entire weight of a plant, plant fat and oil that is used as seed oils at the industrial level may be preferably used, and plant oils are particularly preferable. Plant oils may be simple lipids that is the esters of fatty acids with alcohols, complex lipid including phosphorus, sugar, nitrogen, and the like, or a fatty acid. An alcohol of a simple lipid may be a higher alcohol having a high molecular weight or a polyhydric alcohol, such as glycerol (glycerin). A fatty acid of a simple lipid may be a saturated fatty acid, unsaturated fatty acid, or special fatty acid comprising a hydroxyl group or an epoxy group. Simple lipids that are the esters of glycerol and fatty acid may be monoacylglycerol, diacylglycerol, or triacylglycerol.

Hereafter, substances that improve productivity are described with reference to a fat and oil, although the technical scope of the present invention is not limited thereto. The present invention is also applicable to substances other than the fat and oil as substances generated from plants.

The present invention can cover any plants without particular limitation. Angiosperms are particularly preferable as plants, and either monocotyledonous or dicotyledonous plants may be covered. Plants that have been heretofore used for the production of the fat and oil are particularly preferable. Examples of intended plants include soybeans, sesame, olive oils, coconuts, rice, cottons, sunflowers, maize, safflowers, and rapeseeds. Also, *Arabidopsis thaliana*, which is extensively used as a model organism in genetic analysis of plants and for which a method for gene expression analysis has been established can be intended.

The term "transcription factor with suppressed transcription accelerating activity" refers to a transcription factor having transcription accelerating activity significantly lower than the activity that the transcription factor would naturally have. Methods for lowering transcription accelerating activity are not particularly limited. Gene-silencing techniques can be extensively employed, and a method of constructing a fusion protein to which a repressor domain sequence has been added is the most preferable.

In such a technique, "repressor domain sequences" are amino acid sequences constituting peptides that convert arbitrary transcription factors into transcription repressors, and the present inventors have discovered a wide variety of such sequences.

Techniques involving the use of repressor domain sequences are disclosed in, for example, JP Patent Publication (kokai) No. 2001-269177 A, JP Patent Publication (kokai) No. 2001-269178 A, JP Patent Publication (kokai) No. 2001-292776 A, JP Patent Publication (kokai) No. 2001-292777 A, JP Patent Publication (kokai) No. 2001-269176 A, JP Patent Publication (kokai) No. 2001-269179 A, WO 03/055903, Ohta, M., Matsui, K., Hiratsu, K., Shinshi, H. and Ohme-Takagi, M., The Plant Cell, Vol. 13, 1959-1968, August, 2001, and Hiratsu, K., Ohta, M., Matsui, K., Ohme-Takagi, M., FEBS Letters 514, 2002, 351-354. Repressor domain sequences are cleaved from Class II ethylene-responsive element binding factor (ERF) proteins or plant zinc finger proteins (e.g., the *Arabidopsis thaliana* SUPERMAN protein) and have very simple structures.

Examples of transcription factors with transcription accelerating activity to be suppressed include the transcription factor identified as At3g25890 in *Arabidopsis thaliana* (hereafter simply referred to as the "transcription factor At3g25890") and the transcription factor identified as At1g56650 in *Arabidopsis thaliana* (hereafter simply referred to as the "transcription factor At1g56650"). The transcription factor At3g25890 is known to belong to the ERF (ethylene response factor) subfamily B-6 of the ERF/AP2 transcription factor family and contain one AP2 domain. The amino acid sequence of the transcription factor At3g25890 is shown in SEQ ID NO: 2. The nucleotide sequence of the gene encoding the transcription factor At3g25890 is shown in SEQ ID NO: 1. The transcription factor At1g56650 is known to encode a putative MYB domain containing a transcription factor involved in anthocyanin metabolim and radical scavenging ability, and it is known to be essential for dihydroflavonol reductase gene expression. The amino acid sequence of the transcription factor At1g56650 is shown in SEQ ID NO: 4. The nucleotide sequence of the gene encoding the transcription factor At1g56650 is shown in SEQ ID NO: 3.

Transcription factors At3g25890 and At1g56650 with transcription accelerating activity to be suppressed are not limited to those comprising the amino acid sequences as shown in SEQ ID NOs: 2 and 4. An intended transcription factor may be a transcription factor comprising an amino acid sequence derived from the amino acid sequences as shown in SEQ ID NOs: 2 and 4 by deletion, substitution, addition, or insertion of 1 or a plurality of amino acids and having transcription accelerating activity. The number of such plurality of amino acids is, for example, 1 to 20, preferably 1 to 10, more preferably 1 to 7, further preferably 1 to 5, and particularly preferably 1 to 3. Deletion, substitution, or addition of amino acids can be conducted by modifying a nucleotide sequence encoding the above-mentioned transcription factor via a method known in the art. Mutation can be introduced into a nucleotide sequence via known methods, such as the Kunkel or Gapped duplex method, or methods in accordance therewith. For example, mutation is introduced with the use of mutagenesis kits utilizing site-directed mutagenesis (e.g., Mutant-K or Mutant-G (tradenames, manufactured by TAKARA)) or the LA PCR in vitro Mutagenesis Series Kit (tradename, manufactured by TAKARA).

Further, transcription factors with transcription accelerating activity to be suppressed are not limited to transcription factors At3g25890 and At1g56650 in *Arabidopsis thaliana*, and transcription factors (hereafter referred to as "homologous transcription factors) having equivalent functions in plants other than *Arabidopsis thaliana* (e.g., plants mentioned above) are within the scope of the present invention. The homologous transcription factor corresponding to the transcription factor At3g25890 or At1g56650 can be searched for can be searched for, in case that the plant genome information has been revealed, using the genome information of the intended plant based on the amino acid sequences of the transcription factor At3g25890 or At1g56650 or the nucleotide sequences of the genes. As a homologous transcription factor, an amino acid sequence having, for example, 70% or higher, preferably 80% or higher, more preferably 90% or higher, and most preferably 95% or higher homology to the amino acid sequence of the transcription factor At3g25890 or At1g56650 is searched for. Homology values are determined by default using a computer program that implements the BLAST algorithm and a database that stores gene sequence information.

In case that the genome information of intended plants has not been revealed, the genome is extracted from the intended plant, or a cDNA library of the intended plant is constructed. The genome region or cDNA hybridizing under stringent conditions to at least part of the nucleotide sequence of the gene of transcription factor At3g25890 or At1g56650 is then isolated. Thus, a homologous gene can be identified. Under stringent conditions, hybridization is carried out via washing at 60° C. in the presence of 2×SSC while maintaining a bond. Hybridization can be carried out in accordance with a conventional technique, such as the method disclosed by J. Sambrook et al. Molecular Cloning, A Laboratory Manual, 2nd Ed., Cold Spring Harbor Laboratory, 1989.

The plant according to the present invention significantly improves the amount of fat and oil production via expression of the above-described transcription factor with suppressed transcription accelerating activity. In such plant, the endogenous transcription factor may be modified and transcription accelerating activity thereof may be suppressed. Alternatively, a gene encoding a modified transcription factor with suppressed transcription accelerating activity may be introduced and such gene may be expressed. Transcription accelerating activity of the gene encoding the target transcription factor may be suppressed via a so-called gene-silencing technique.

A preferable example of such technique is a technique comprising introducing a gene encoding a fusion protein resulting from the fusion of the aforementioned transcription factor with a functional peptide that converts an arbitrary transcription factor into a transcription repressor into an intended plant and expressing such fusion protein therein.

A functional peptide that converts an arbitrary transcription factor into a transcription repressor (hereafter referred to as a "transcription repressor converting peptide") used herein is not particularly limited, as long as it can form a chimeric protein fused with the transcription factor, thereby suppressing transcription of the target gene regulated by the transcription factor. Such transcription repressor converting peptide is described in detail in JP Patent Publication (kokai) No. 2005-204657 A, and all peptides disclosed therein can be used.

Examples of transcription repressor converting peptides include amino acid sequences represented by formulae (1) to (8) below:

(1) X1-Leu-Asp-Leu-X2-Leu-X3 (SEQ ID NO: 9 with deletion of 0-10 residues from the N-terminus)
wherein X1 represents 0 to 10 amino acid residues; X2 represents Asn or Glu; and X3 represents at least 6 amino acid residues;

(2) Y1-Phe-Asp-Leu-Asn-Y2-Y3 (SEQ ID NO: 10 with deletion of 0-10 residues from the N-terminus)
wherein Y1 represents 0 to 10 amino acid residues; Y2 represents Phe or Ile; and Y3 represents at least 6 amino acid residues;

(3) Z1-Asp-Leu-Z2-Leu-Arg-Leu-Z3 (SEQ ID NO: 11 with deletion of 0-10 residues from the C-terminus and deletion of 0-2 residues from the N-terminus)
wherein Z1 represents Leu, Asp-Leu, or Leu-Asp-Leu; Z2 represents Glu, Gln, or Asp; and Z3 represents 0 to 10 amino acid residues;

(4) Asp-Leu-Z4-Leu-Arg-Leu (SEQ ID NO: 12)
wherein Z4 represents Glu, Gln, or Asp;

(5) α1-Leu-β1-Leu-γ1-Leu (SEQ ID NO: 13);
(6) α1-Leu-β1-Leu-γ2-Leu (SEQ ID NO: 14);
(7) α1-Leu-β2-Leu-Arg-Leu (SEQ ID NO: 15); and
(8) α2-Leu-β1-Leu-Arg-Leu (SEQ ID NO: 16)
wherein, in formulae (5) to (8), α1 represents Asp, Asn, Glu, Gln, Thr, or Ser; α2 represents Asn, Glu, Gln, Thr, or Ser; β1 represents Asp, Gln, Asn, Arg, Glu, Thr, Ser, or His; β2 represents Asn, Arg, Thr, Ser, or His; γ1 represents Arg, Gln, Asn, Thr, Ser, His, Lys, or Asp; and γ2 represents Gln, Asn, Thr, Ser, His, Lys, or Asp.

Transcription Repressor Converting Peptide Represented by Formula (1)

The number of amino acid residues represented by X1 of the transcription repressor converting peptide represented by formula (1) may be 0 to 10. Specific types of amino acids that constitute the amino acid residues represented by X1 are not particularly limited, and any amino acid may be used. It is preferable that the number of amino acid residues represented by X1 be as small as possible from the viewpoint of ease of synthesis of the transcription repressor converting peptide represented by formula (1). Specifically, the number of amino acid residues represented by X1 is preferably 5 or less.

Also, the number of the amino acid residues represented by X3 of the transcription repressor converting peptide represented by formula (1) may be at least 6. Specific types of amino acids that constitute the amino acid residues represented by X3 are not particularly limited, and any amino acid may be used.

Transcription Repressor Converting Peptide Represented by Formula (2)

The number of amino acid residues represented by Y1 of the transcription repressor converting peptide represented by formula (2) may be 0 to 10 as in the case of X1 of the transcription repressor converting peptide represented by formula (1). Also, specific types of amino acids that constitute the amino acid residues represented by Y1 are not particularly limited, and any amino acid may be used. Specifically, the number of amino acid residues represented by Y1 is preferably 5 or less.

Also, the number of the amino acid residues represented by Y3 of the transcription repressor converting peptide represented by formula (2) may be at least 6, as in the case of X3 of the transcription repressor converting peptide represented by formula (1). Also, specific types of amino acids that constitute the amino acid residues represented by Y3 are not particularly limited, and any amino acid may be used.

Transcription Repressor Converting Peptide Represented by Formula (3)

The amino acid residues represented by Z1 of the transcription repressor converting peptide represented by formula (3) comprise 1 to 3 Leu residues: i.e., Leu when the number of amino acids is 1; Asp-Leu when the number of amino acids is 2; and Leu-Asp-Leu when the number of amino acids is 3.

In contrast, the number of the amino acid residues represented by Z3 of the transcription repressor converting peptide represented by formula (3) may be 0 to 10. Also, specific types of amino acids that constitute the amino acid residues represented by Z3 are not particularly limited, and any amino acid may be used. Specifically, the number of amino acid residues represented by Z3 is more preferably 5 or less. Specific examples of amino acid residues represented by Z3 include, but are not limited to, Gly, Gly-Phe-Phe, Gly-Phe-Ala, Gly-Tyr-Tyr, and Ala-Ala-Ala.

The number of amino acid residues constituting the entire transcription repressor converting peptide represented by formula (3) is not particularly limited. From the viewpoint of ease of synthesis, the number of amino acids is preferably 20 or less.

Transcription Repressor Converting Peptide Represented by Formula (4)

The transcription repressor converting peptide represented by formula (4) is a hexamer (6-mer) comprising 6 amino acid residues. When the amino acid residue represented by Z4 of the transcription repressor converting peptide represented by formula (4) is Glue, the amino acid sequence of interest is equivalent to the amino acid sequence composed of amino acids 196 to 201 of the *Arabidopsis thaliana* SUPERMAN protein (SUP protein).

Various transcription repressor converting peptides described above can fuse to the above-described transcription factors to result in fusion proteins, and such peptides can convert the transcription factors into transcription repressors. According to the present invention, therefore, fusion proteins can be produced using polynucleotides encoding the transcription repressor converting peptides to obtain fusion genes thereof with genes encoding the transcription factors.

More specifically, polynucleotides encoding the transcription repressor converting peptides (hereafter referred to as the "transcription repressor converting polynucleotides") are ligated to the genes encoding the transcription factors to construct fusion genes, and the resulting fusion genes are introduced into plant cells. Thus, fusion proteins can be produced. Specific nucleotide sequences of the transcription repressor converting polynucleotides are not particularly limited, and such polynucleotides may comprise nucleotide sequences corresponding to the amino acid sequences of the transcription repressor converting peptides based on genetic codes. The transcription repressor converting polynucleotides may comprise nucleotide sequences that serve as ligation sites to be connected to the transcription factor genes, as necessary. When the amino acid reading frame of the transcription repressor converting polynucleotide is not aligned with that of the transcription factor gene, the polynucleotide may further comprise an additional nucleotide sequence, so as to align the reading frames. Further, the polynucleotide may comprise various additional polypeptides, such as a polypeptide having a linker function for connecting the transcription factor to the transcription repressor converting peptide or a polypeptide for labeling a fusion protein with an epitope, such as His, Myc, or Flag. Further, the fusion protein may comprise a structure other than a polypeptide, such as a sugar chain or an isoprenoid group, according to need.

The method for producing the plant according to the present invention is not particularly limited, provided that the method comprises a step of producing a transcription factor with suppressed transcription accelerating activity in a plant to improve the productivity of a fat and oil. An example thereof is a production method comprising steps of construction of an expression vector, transformation, and selection. Such steps are described in detail below.

A step of constructing an expression vector is not particularly limited, provided that a recombinant expression vector comprising the gene encoding the above-mentioned transcription factor, the transcription repressor converting polynucleotide, and a promoter is constructed. A variety of known vectors can be used as bases for recombinant expression vectors. Examples of vectors that can be used include plasmid, phage, and cosmid vectors, and adequate vectors can be selected in accordance with the plant cells to which such vectors are introduced or methods of introduction into a cell. Specific examples include pBR322, pBR325, pUC19, pUC119, pBluescript, pBluescriptSK, and pBI vectors. When a vector is introduced into plant by the *Agrobacterium* method, in particular, use of the pBI binary vector is preferable. Specific examples of pBI binary vectors include pBIG, pBIN19, pBI101, pBI121, and pBI221 vectors.

Promoters are not particularly limited, provided that such promoters can express a gene of interest in a plant. Known promoters can be preferably used. Examples of such promoters include cauliflower mosaic virus 35S promoters (CaMV 35S), actin promoters, ubiquitin promoters, noparin synthase promoters, tobacco PR1a gene promoters, and ribulose-1,5- bisphosphate carboxylase/oxygenase small subunit promoters in tomatoes. Among such promoters, cauliflower mosaic virus 35S promoters, actin promoters, and ubiquitin promoters are preferable. With the use of such promoters, arbitrary genes can be intensively expressed upon introduction of the resulting recombinant expression vector into plant cells. A promoter is ligated so as to express the fusion gene of the gene encoding the transcription factor with the transcription repressor converting polynucleotide, and the resultant may be introduced into the vector in that state. The specific structure of a recombinant expression vector is not particularly limited.

The recombinant expression vector may further comprise other DNA segments, in addition to the promoter and the fusion gene. Such other DNA segments are not particularly limited, and examples thereof include a terminator, a selection marker, an enhancer, and a nucleotide sequence for enhancing translation efficiency. Also, the recombinant expression vector may further comprise a T-DNA region. The T-DNA region can enhance the efficiency of gene introduction, particularly when introducing the recombinant expression vector into a plant with the use of *Agrobacterium*.

A terminator is not particularly limited, provided that it functions as a transcription termination site, and a known terminator may be used. Specific examples of terminators that can be preferably used include the transcription termination region of the noparin synthase gene (the Nos terminator) and the transcription termination region of the cauliflower mosaic virus 35S (the CaMV 35S terminator), with the Nos terminator being preferable. The recombinant vector can be used to avoid the occurrence of phenomena such as synthesis of an unnecessarily long transcript after the introduction thereof into plant cells or a reduction in the plasmid copy number caused by a potent promoter by positioning a terminator in an adequate site.

Drug-resistance genes can be used as selection markers, for example. Specific examples of such drug-resistance genes include drug-resistance genes that are resistant to hygromycin, bleomycin, kanamycin, gentamicin, and chloramphenicol. Plants that grow in a medium containing the above antibiotics may be selected with the use of such selection markers, so that transformed plants can be easily selected.

An example of a nucleotide sequence for enhancing translation efficiency is the omega sequence derived from the tobacco mosaic virus. This omega sequence may be located in the untranslational region (5' UTR) of the promoter to enhance the translation efficiency of the fusion gene. Thus, the recombinant expression vector can comprise a variety of DNA segments in accordance with its intended purposes.

Methods for constructing recombinant expression vectors are not particularly limited. The promoter, the gene encoding the transcription factor, the transcription repressor converting polynucleotide, and, according to need, other DNA segments may be introduced into an adequately selected matrix vector in a predetermined order. For example, the gene encoding the transcription factor may be ligated to the transcription repressor converting polynucleotide to construct a fusion gene, the fusion gene may then be ligated to the promoter (e.g., a terminator according to need) to construct an expression cassette, and the resulting expression cassette may be introduced into the vector.

When constructing a fusion gene and an expression cassette, for example, cleavage sites of DNA segments are made to be protruding ends that are complementary to each other, such DNA segments are subjected to the reaction with the aid of ligation enzymes, and the order of such DNA segments can be determined. When an expression cassette comprises a terminator, the expression cassette may comprise the promoter, the chimeric gene, and the terminator, in that order from upstream. Also, the types of reagents used for constructing a recombinant expression vector (i.e., restriction enzymes or ligation enzymes) are not particularly limited, and commercially available products may be adequately selected and used.

Also, methods for growing the recombinant expression vector (i.e., methods of production) are not particularly limited, and known methods can be employed. In general, *E. coli* hosts may be used, and the recombinant expression vector may be grown therein. In such a case, preferable *E. coli* species may be selected in accordance with a vector type.

Step of Transformation

The step of transformation that is carried out in the present invention comprises introducing the recombinant expression vector into a plant cell in order to express the aforementioned fusion genes. Methods of introducing a recombinant expression vector into a plant cell (i.e., methods of transformation) are not particularly limited, and adequate known methods can be employed in accordance with a given plant cell. Specific examples of such methods include a method involving the use of *Agrobacterium* and a method involving direct introduction of a recombinant expression vector into a plant cell. Examples of methods involving the use of *Agrobacterium* that can be employed include methods described in Bechtold, E., Ellis, J., and Pelletier, G., 1993, In Planta *Agrobacterium*-mediated gene transfer by infiltration of adult *Arabidopsis* plants, C. R. Acad. Sci. Paris Sci. Vie, 316, 1194-1199 and Zyprian E., Kado C. L., *Agrobacterium*-mediated plant transformation by novel mini-T vectors in conjunction with a high-copy vir region helper plasmid, Plant Molecular Biology, 1990, 15 (2), 245-256.

Examples of methods involving direct introduction of a recombinant expression vector into a plant cell include microinjection, electroporation, the polyethylene glycol method, the particle gun method, the protoplast fusion method, and the calcium phosphate method.

Examples of plant cells into which the recombinant expression vector is to be introduced include tissue cells in plant organs such as flowers, leaves, and roots, calluses, and suspension cultured cells. According to the method for producing plants according to the present invention, the recombinant expression vector may be adequately constructed in accordance with the type of plant to be produced. Alternatively, a general-purpose recombinant expression vector may be constructed in advance and it may be introduced into a plant cell. Specifically, the method for producing plants according to the present invention may or may not comprise the step of constructing the recombinant expression vector.

Other Steps and Other Methods

The method for producing the plant according to the present invention may comprise a method of transformation. Further, the method may comprise a method for constructing a recombinant expression vector and other steps. Specifically, the method may comprise a step of selecting adequate transformants from transformed plants.

Methods of selection are not particularly limited. For example, transformants may be selected based on, for example, drug resistance, such as hygromycin-resistance, or based on the content of fat and oil in plants or arbitrary organs or tissues after the transformed plants have been grown. For example, transformants may be selected based on fat and oil content by quantifying the fat and oil components in seeds of the transformants in accordance with a conventional technique and comparing the quantified value with the fat and oil content in seeds of non-transformed plants (see the examples below).

According to the method for producing the plant according to the present invention, the fusion gene is introduced into a plant. Thus, offspring plants exhibiting significantly improved fat and oil content can be obtained from such plant via sexual or asexual reproduction. Also, plant cells or reproductive materials, such as seeds, fruits, stocks, calluses, tubers, cut ears, or lumps, may be obtained from a plant or an offspring plant thereof, and a plant of interest can be mass-produced therefrom. The method for producing the plant according to the present invention, accordingly, may comprise a step of growing the selected plant (i.e., the step of mass production).

The term "plant" used herein refers to a grown plant, a plant cell, a plant tissue, a callus, or a seed. According to the present invention, specifically, substances that can eventually grow into individual plants are regarded as plants. Plant cells can exist in various forms. Examples of such plant cells include suspension cultured cells, protoplasts, and leaf sections. Such plant cells may be grown and differentiated to obtain plants. Plants can be reproduced from plant cells via a known technique in accordance with plant cell type. The method for producing the plant according to the present invention, accordingly, may comprise a step of reproducing plants from plant cells or the like.

The method for producing the plant according to the present invention is not limited to a method in which transformation is carried out with the aid of a recombinant expression vector, and other methods may be employed. Specifically, a fusion protein may be introduced into a plant, for example. In such a case, a fusion protein may be introduced into a young plant so as to improve the fat and oil content in a site of a plant that is to be eventually used. Methods for introducing a fusion protein are not particularly limited, and various known methods may be employed.

As described above, the present invention can provide a plant into which a transcription factor with suppressed transcription accelerating activity has been introduced and in which fat and oil content has been significantly improved. A transcription factor having transcription accelerating activity is also expressed in the plant according to the present invention; however, the transcription factor with suppressed transcription accelerating activity can suppress gene expression in a dominant-negative manner. This varies the expression levels of genes involved in fat and oil production and/or genes involved in decomposition of the produced fat and oil in the plant according to the present invention. This can result in the significantly enhanced fat and oil content.

The condition of "significantly enhanced fat and oil content" refers to a situation in which fat and oil content has been enhanced, although seed mass per grain has not changed compared with wild-type plants, or a situation in which fat and oil content has been enhanced with significantly increased seed mass per grain compared with wild-type plants. Both cases indicate increased amounts of fat and oil produced by an individual plant. The plant according to the present invention can be used for the method for producing plant-derived fat and oil. For example, the plant according to the present invention is allowed to grow, seeds are collected, and fat and oil components are extracted from the collected seeds. Thus, the fat and oil can be produced.

It can be said that the method for producing fat and oil utilizing the plant according to the present invention is excellent particularly in terms of productivity because of the high fat and oil content in an individual plant. If the number of cultivated plants is assumed to be constant per unit of cultivation area, specifically, the amount of fat and oil produced per unit of cultivation area is significantly increased with the use of the plant according to the present invention. With the use of the plant according to the present invention, accordingly, production costs required for the production of fat and oil can be remarkably reduced.

In the method for producing fat and oil using the plant according to the present invention, the fat and oil to be produced are not particularly limited. Examples thereof include plant-derived fat and oil, such as soybean oil, sesame oil, olive oil, coconut oil, rice oil, cottonseed oil, sunflower oil, corn oil, safflower oil, and rapeseed oil. The produced fat and oil can be extensively used for household or industrial applications. Further, such fat and oil can be used as starting materials for biodiesel fuels. With the use of the plant according to the present invention, specifically, such fat and oil for household or industrial applications, biodiesel fuels, and the like can be produced at low cost. An improved seed yield per plant can result in an improvement in the productivity of feeds and food products, in addition to the productivity of fat and oil, and production costs can be reduced. Also, an increased amount of biomass per plant can result in an improvement in the productivity of biomass after seed harvesting or the entire biomass. Biomass can be adequately treated to be degraded into sugar. Sugar can be converted into a variety of chemical substances, including ethanol, by a fermentation method utilizing microorganisms. Also, biomass may be directly combusted to obtain thermal energy or an electric energy may be obtained from the thermal energy. With the use of the plant provided by the present invention, chemical substances, thermal energy, electric energy, and the like described above can be produced in a cost-effective manner.

EXAMPLES

Hereafter, the present invention is described in greater detail with reference to the examples, although the technical scope of the present invention is not limited to the examples.

Example 1

In this example, fusion proteins of *Arabidopsis thaliana* transcription factors At3g25890 and At1g56650 to which repressor domain sequences had been added were expressed in plants, and the fat and oil content of the seeds obtained from the plants was measured.

Amplification of Transcription Factor Genes

The genes encoding the transcription factor At3g25890 and the gene encoding the transcription factor At1g56650 were obtained from the *Arabidopsis thaliana* cDNA library, and the regions excluding the termination codons of such genes were amplified via PCR using the primers shown below. PCR was carried out via denaturation at 94° C. for 1 minute, annealing at 47° C. for 2 minutes, and elongation at 74° C. for 1 minute, and this cycle was repeated 25 times. After the completion of PCR, the amplified DNA fragment was separated via agarose gel electrophoresis and recovered.

```
Forward primer for amplifying At3g25890
ATGGCTGAACGAAAGAAACGC         (SEQ ID NO: 5)

Reverse primer for amplifying At3g25890
TGGGCACGCGATATTAAGAGG         (SEQ ID NO: 6)

Forward primer for amplifying At1g56650
GATGGAGGGTTCGTCCAAAGGGC       (SEQ ID NO: 7)

Reverse primer for amplifying At 1 g56650
ATCAAATTTCACAGTCTCTCCATCG     (SEQ ID NO: 8)
```

Preparation of Fusion Genes

Fusion genes that encode fusion proteins of the transcription factor At3g25890 and the transcription factor At1g56650 each comprising a repressor domain sequence added to the C terminus were prepared. In order to add a polynucleotide encoding a repressor domain sequence to the 3' terminus of each of the DNA fragments amplified via PCR above, the p35SSXG vector having the SmaI site and a polynucleotide encoding the repressor domain sequence (GLDLDLELRLGFA; SEQ ID NO: 17) in a site downstream of the CaMV 35S promoter was first prepared. p35SSXG was cleaved with SmaI and the DNA fragments amplified via PCR above were inserted thereinto. The resulting expression vectors were designated as p35SSXG (At3g25890) and p35SSXG (At1g56650).

Construction of Binary Vectors

A pBCKH binary vector was used in order to transform a plant by the *Agrobacterium* method. This vector was prepared by incorporating a cassette of the Gateway vector conversion system (Invitrogen) into the HindIII site of pBIG (Hygr) (Nucleic Acids Res. 18, 203, 1990). In order to incorporate the fusion gene into this vector, the vector was mixed with p35SSXG (At3g25890) or p35SSXG (At1g56650), and a recombination reaction was carried out using GATEWAY LR clonase (Invitrogen). As a result, pBCKH-p35SSXG (At3g25890) and pBCKH-p35SSXG (At1g56650) were constructed.

Introduction of Binary Vector into Plant

In this example, a dicotyledonous plant *Arabidopsis thaliana* of Brassicaceae (*Arabidopsis thaliana*, Columbia) was used. Gene introduction was carried out in accordance with the method described in Bechtold, E., Ellis, J., and Pelletier, G., 1993, In Planta *Agrobacterium*-mediated gene transfer by infiltration of adult *Arabidopsis* plants, C. R. Acad. Sci. Paris Sci. Vie, 316, 1194-1199 and Zyprian E., Kado C. L., *Agrobacterium*-mediated plant transformation by novel mini-T vectors in conjunction with a high-copy vir region helper plasmid, Plant Molecular Biology, 1990, 15 (2), 245-256. Plants were infected via soaking in the *Agrobacterium* solution without depressurization. Specifically, pBCKH-p35SSXG (At3g25890) and pBCKH-p35SSXG (At1g56650) binary vectors were introduced into soil bacteria (i.e., the *Agrobacterium tumefaciens* strain GV3101 (C58C1Rifr) pMP90 (Gmr)) (koncz and Schell, 1986) via electroporation. The introduced bacteria were cultured in 1 liter of YEP medium containing antibiotics (50 µg/ml of kanamycin (Km), 25 µg/ml of gentamicin (Gm), and 50 µg/ml of rifampicin (Rif)) until OD600 reached 1. Subsequently, the bacteria were recovered from the culture solution and suspended in 1 liter of infiltration medium (containing 2.2 g of MS salt, 1× B5 vitamins, 50 g of sucrose, 0.5 g of MES, 0.044 µM of benzylaminopurine, and 400 µl of Silwet per liter; pH: 5.7).

The *Arabidopsis thaliana* plant that had been grown for 14 days was soaked in this solution for 1 minute, the plant was infected, and culture was continued again for fructification. The resulting seeds (T1 seeds) were sterilized with a 50% bleach/0.02% Triton X-100 solution for 7 minutes, the seeds were rinsed three times with sterilized water, and the seeds were sowed on the sterilized hygromycin selection medium (4.3 g/l MS salts, 0.5% sucrose, 0.5 g/l MES (pH 5.7), 0.8% agar, 30 mg/l hygromycin, and 250 mg/l vancomycin). Ten transformed strains that had grown on the hygromycin plate (T1 plants) were selected per modified transcription gene and transferred to a pot (diameter: 50 mm) containing vermiculite composite soil. The transformants were cultivated at 22° C. for 16 hours in the light and 8 hours in the dark at an optical intensity of about 60 to 80 µE/cm$^2$ to obtain seeds (T2 seeds).

<Analysis of T2 Seeds>

Quantitative analysis of fat and oil components in the resulting T2 seeds was carried out using MARAN-23 (Resonance Insturuments Ltd., UK)$^H$-NMR and the RI-NMR Ver. 2.0 analysis software. With the use of such apparatuses, 2 to 10 mg of T2 seeds were measured. A calibration curve was prepared using olive oil as the fat and oil reference material and the fat and oil content in the seeds (% by weight) was determined.

Single seed weight was measured by weighing about 1 mg of T2 seeds, spreading the T2 seeds on a glass petri dish, scanning the image of seeds using Pictrostat (Fujifilm), gray-scale processing the image using Photoshop image-editing software, analyzing the gray-scale image using Scion Image image-analyzing software, and determining the number of seeds. The total seed weight was divided by the number of seeds, and the seed weight per grain was determined. The fat and oil components of wild-type *Arabidopsis thaliana* were similarly quantified. The results are summarized in Table 1.

TABLE 1

| Name of introduced gene | Fat and oil content | | Single seed weight | | Fat and oil amount per grain | |
|---|---|---|---|---|---|---|
| | Content (%) | Percentage of increase | Weight (µg) | Percentage of increase | Amount of fat and oil (µg/grain) | Percentage of increase |
| WT | 36.1 | — | 19.7 | — | 7.2 | — |
| At1g56650-SRDX | 48.2 | 33.5 | 38.8 | 96.5 | 14.8 | 106.3 |
| At3g25890-SRDX | 37.4 | 3.6 | 39.2 | 98.7 | 12.5 | 74.4 |

As is apparent from Table 1, the fat and oil content in the plant into which the transcription factor At1g56650 with suppressed expression accelerating activity had been introduced was much higher than that in wild-type plants and exhibited excellent percentages of increase in fat and oil content per grain (i.e., 106.3%). In the plant into which the transcription factor At3g25890 with suppressed expression accelerating activity had been introduced, the fat and oil content was increased by about 3.6% from wild-type plants, and the seed weight per grain was much higher than that in wild-type plants. As a result, the percentage of increase in fat and oil content per grain was as high as 74.4%.

<Analysis of T3 Seeds>

In order to analyze T3 seeds, the T2 plants prepared as above were cultivated. After the T2 seeds were sterilized with a 50% bleach/0.02% Triton X-100 solution for 7 minutes, the seeds were rinsed three times with sterilized water, and the seeds were sowed on the sterilized seeding medium (4.3 g/l MS salts, 0.5% sucrose (pH 5.7), 0.8% agar, and 10 mg/l hygromycin). Three weeks after seeding, 6 each individuals of the grown gene-introduced plants and the transformed plants (T1 plants) per modified transcription gene were transferred to a pot (diameter: 50 mm) containing vermiculite composite soil. As controls, 4 non-recombinant *Arabidopsis thaliana* plants were transferred. The plants were cultivated at 22° C. for 16 hours in the light and 8 hours in the dark at an optical intensity of about 30 to 45 µE/cm², and, 4 weeks thereafter, the plants were subjected to thinning out while leaving 4 recombinant plants and 3 non-recombinant plants behind. The plants were cultivated for an additional 7 weeks until 11 weeks after the transfer. The T3 plant of the plant into which the transcription factor At1g56650 with suppressed expression accelerating activity had been introduced was designated as TP107, and the T3 plant of the plant into which the transcription factor At3g25890 with suppressed expression accelerating activity had been introduced was designated as CR029.

Figure 2:
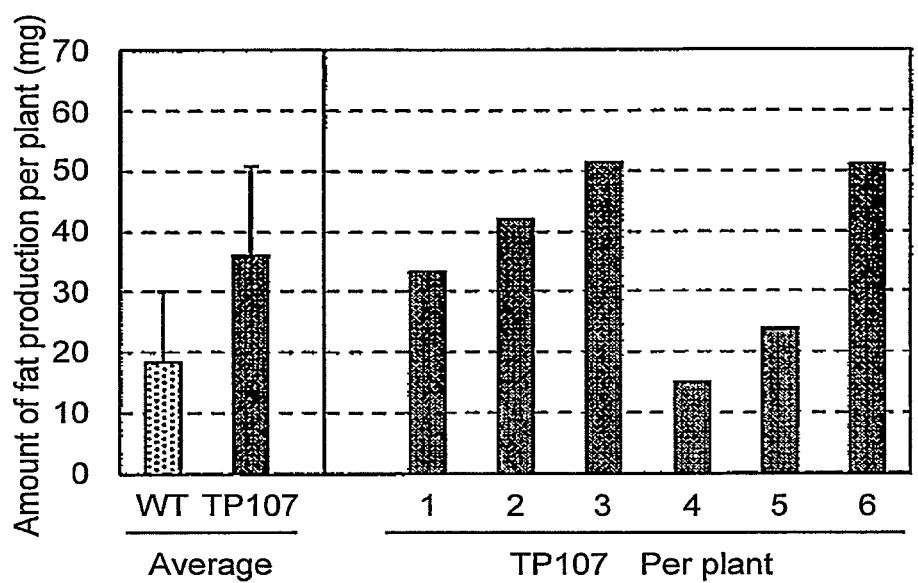
FIG. 2 is a characteristic diagram showing the results of measuring the amount of fat and oil production per individual plant in the T2 plant-T3 seeds (TP107) of a plant into which the transcription factor (At1g56650) with suppressed expression accelerating activity has been introduced.

The aerial parts of the plants were introduced into a paper bag and dried at 22° C. and humidity of 60% for 2 weeks. Thereafter, total biomass amount and seed yield were weighed using an electronic balance. Quantitative analysis of fat and oil was carried out by the method described above. The results are shown in FIG. 1, FIG. 2, Table 2, and Table 3. In Table 2, the symbol "*" indicates the value of an individual exhibiting the highest analytical value.

expression accelerating activity had been introduced (i.e., T2 generation plants, T3 generation seeds) and the plants into which the transcription factor At1g56650 with suppressed expression accelerating activity had been introduced (i.e., T2 generation plants, T3 generation seeds), in comparison with those of wild-type plants. Also, the yield index (i.e., percentage allocation to seeds) of such plants was significantly improved in comparison with that of wild-type plants.

The above results demonstrate that the plants into which the transcription factor At3g25890 with suppressed expression accelerating activity had been introduced (i.e., T2 generation plants, T3 generation seeds) and the plants into which the transcription factor At1g56650 with suppressed expression accelerating activity had been introduced (i.e., T2 generation plants, T3 generation seeds) exhibit excellent fat and oil content per grain and excellent yield index per unit of cultivation area. Thus, these plants were found to be very effective for fat and oil production.

When the T2 generation is compared with the T3 generation, the above results occasionally show differences in fat

TABLE 2

| Tested strain | | | Fat and oil content per plant | | Seed yield | | Fat and oil content | |
|---|---|---|---|---|---|---|---|---|
| | | | Amount of fat and oil (mg) | Percentage of increase | Seed yield (mg) | Percentage of increase | Content (%) | Percentage of increase |
| WT1 | n = 4 | Average | 16.6 | — | 58.7 | — | 27.8 | — |
| At3g25890-SRDX (CR029) | n = 4 | Max.* | 63.4 | 273% | 205.0 | 249% | 30.5 | 11% |
| | | Average | 32.2 | 95% | 105.1 | 79% | 28.1 | 1% |
| WT2 | n = 4 | Average | 18.4 | — | 65.0 | — | 27.5 | — |
| At1g56650-SRDX (TP107) | n = 4 | Max.* | 51.4 | 180% | 163.0 | 151% | 31.5 | 15% |
| | | Average | 36.2 | 98% | 122.0 | 88% | 29.1 | 5% |

As is apparent from FIG. 1, FIG. 2, and Table 2, transformed plants exhibiting the excellent percentage of increase in fat and oil content per individual plant of 273% of that of wild-type plants were obtained from plants into which the transcription factor At3g25890 with suppressed expression accelerating activity had been introduced (i.e., T2 generation plants, T3 generation seeds). The percentage of increase was 95% on average. Also, transformed plants exhibiting the excellent percentage of increase in fat and oil content per individual plant of 180% of that of wild-type plants were obtained from plants into which the transcription factor At1g56650 with suppressed expression accelerating activity had been introduced (i.e., T2 generation plants, T3 generation seeds). The percentage of increase was 98% on average.

and oil content per plant, seed yield, fat and oil content, and the amount of biomass. Because of the application of Mendel's law for the case of the difference between the T2 generation and the T3 generation, the T2 generation and the T3 generation do not always have the same genotype. Since mRNA may suppress gene expression as is known in the case of the RNAi technique, also, differences occur between the T2 generation and the T3 generation. The plants into which the transcription factor At3g25890 with suppressed expression accelerating activity had been introduced and the plants into which the transcription factor At1g56650 with suppressed expression accelerating activity had been introduced

TABLE 3

| Tested strain | | Amount of biomass | | Seed yield | | Yield index | | Fat and oil content | | Amount of fat and oil per individual | |
|---|---|---|---|---|---|---|---|---|---|---|---|
| | | Amount of biomass (mg) (A) | Percentage of increase | Seed yield (mg) (B) | Percentage of increase | Yield index B/A | Percentage of increase | Fat and oil content (%) | Percentage of increase | Amount of fat and oil per individual (mg) | Percentage of increase |
| WT1 | n = 4 | 403.6 | — | 113.3 | — | 0.274 | — | 29.6 | — | 34.1 | — |
| At3g25890-SRDX (CR029) | n = 6 | 479.2 | 19% | 155.6 | 37% | 0.319 | 16% | 32.5 | 10% | 51.3 | 51% |
| WT2 | n = 4 | 440.5 | — | 126.3 | — | 0.288 | — | 30.3 | — | 38.3 | — |
| At1g56650-SRDX (TP107) | n = 6 | 547.1 | 24% | 166.9 | 32% | 0.305 | 6% | 33.5 | 11% | 55.9 | 46% |

As is apparent from Table 3, the amount of biomass and the seed yield were significantly improved in the plants into which the transcription factor At3g25890 with suppressed can be evaluated as exhibiting excellent effects in terms of increased biomass amount, increased seed yield, and increased fat and oil yield.

Example 2

In Example 2, a fusion protein of the *Arabidopsis thaliana* transcription factor At1g56650 to which a repressor domain sequence had been added was expressed in plants as in the case of Example 1, and the fat and oil content in seeds obtained from rice of graminaceous monocotyledonous plants (*Oryza sativa Nipponbare*) was measured.

Amplification of Transcription Factor Gene, Preparation of Fusion Gene, and Construction of Binary Vector Amplification of the transcription factor gene, preparation of the fusion gene, and construction of the binary vector were carried out in the same manner as in Example 1.

Introduction of Binary Vector into Plant

A binary vector was introduced into rice plants (*Nipponbare*) using *Agrobacterium* carrying the binary vector in accordance with the method described in JP Patent No. 3141084 to obtain calluses.

The calluses into which the gene had been introduced were subjected to selection with hygromycin at 50 ppm for a month, and calluses exhibiting drug resistance were obtained. DNA was prepared from the obtained calluses in accordance with a conventional technique. The At1g56650 fusion gene was confirmed via PCR using the prepared DNA as a template. The calluses having drug-resistance phenotypes and containing the At1g56650 fusion gene were transferred to a redifferentiation medium (described in JP Patent No. 3141084) to induce redifferentiation, and the resultant was then transferred to a hormone-free MS medium (described in JP Patent No. 3141084) to obtain transformed plants.

The transformed plants were grown for 16 hours in the light (photon amount: 135 µE/cm$^2$; temperature: 30° C.) and for 8 hours in the dark (temperature: 25° C.) for 100 days. Thereafter, the plants were further grown for 12 hours in the light (photon amount: 135 µE/cm$^2$; temperature: 30° C.) and for 12 hours in the dark (temperature: 25° C.), and the fructified seeds (T1 seeds) were recovered.

Analysis of T1 Seeds

Fat and oil in the resulting rice T1 seeds was quantitatively analyzed in the same manner as in <Analysis of T2 seeds> in Example 1. Since the rice seed weight is about 20 mg per brown rice grain, the fat and oil content in a grain was quantified with good reproducibility. The results are shown in Table 4. Brown rice is a seed containing a pericarp, a seed coat, an albumen, and an aleurone layer, and caryopsis is a so-called hull.

TABLE 4

| Name of introduced gene | Name of strain | Tissue | Fat and oil content Content (%) | Percentage of increase | Single seed weight Weight (mg) | Percentage of increase | Fat and oil amount per grain Fat and oil amount (mg) | Percentage of increase |
|---|---|---|---|---|---|---|---|---|
| WT (average of 5 grains) | | Brown rice | 2.17 | — | 20.9 | — | 0.454 | — |
| At1g56650-SRDX | TP107-3-3 | Brown rice | 4.89 | 125% | 17.8 | −15% | 0.870 | 91.9% |
| At1g56650-SRDX | TP107-5-1 | Brown rice | 2.58 | 19% | 22.5 | 6% | 0.581 | 28.0% |
| WT (average of 5 grains) | | Caryopsis | 5.91 | — | 3.99 | — | 0.236 | — |
| At1g56650-SRDX | TP107-7-5 | Caryopsis | 9.08 | 54% | 3.77 | −6% | 0.342 | 45.2% |
| At1g56650-SRDX | TP107-11-1 | Caryopsis | 9.04 | 53% | 3.40 | −15% | 0.307 | 30.3% |

As is apparent from Table 4, graminaceous monocotyledonous plants into which the transcription factor At1g56650 with suppressed expression accelerating activity had been introduced exhibited a fat and oil content much higher than that of wild-type plants. Such transformed plants exhibited the excellent percentages of increase in fat and oil content per grain of 91.9% in brown rice and 45.2% in caryopsis.

All publications, patents, and patent applications cited herein are incorporated herein by reference in their entirety.

The invention claimed is:

1. A rice plant which expresses a chimeric protein, said chimeric protein comprising a transcription factor fused to a repressor domain sequence that converts said transcription factor into a transcription repressor,
   wherein said transcription factor is selected from the group consisting of (a) and (b):
   (a) a protein comprising the amino acid sequence of SEQ ID NO: 4; and
   (b) a protein comprising the amino acid sequence of SEQ ID NO: 4 but in which 1-20 amino acids have been deleted, substituted, added or inserted,
   and wherein the seeds of said rice plant exhibit an increase in weight, an increase in amount of fat and oil, or an increase in fat and oil content, in comparison to a wild-type rice plant not expressing said chimeric protein.

2. The plant according to claim 1, wherein the repressor domain sequence comprises an amino acid sequence selected from the group consisting of (1) to (8):
   (1) X1-Leu-Asp-Leu-X2-Leu-X3 (SEQ ID NO: 9 with deletion of 0-10 residues from the N-terminus)
   wherein X1 represents 0 to 10 amino acid residues; X2 represents Asn or Glu; and X3 represents at least 6 amino acid residues;
   (2) Y1-Phe-Asp-Leu-Asn-Y2-Y3 (SEQ ID NO: 10 with deletion of 0-10 residues from the N-terminus)
   wherein Y1 represents 0 to 10 amino acid residues; Y2 represents Phe or Ile; and Y3 represents at least 6 amino acid residues;
   (3) Z1-Asp-Leu-Z2-Leu-Arg-Leu-Z3 (SEQ ID NO: 11 with deletion of 0-10 residues from the C-terminus and deletion of 0-2 residues from the N-terminus)

wherein Z1 represents Leu, Asp-Leu, or Leu-Asp-Leu; Z2 represents Glu, Gln, or Asp; and Z3 represents 0 to 10 amino acid residues;

(4) Asp-Leu-Z4-Leu-Arg-Leu (SEQ ID NO: 12) wherein Z4 represents Glu, Gln, or Asp;

(5) α1-Leu-β1-Leu-γ1-Leu (SEQ ID NO: 13);
(6) α1-Leu-β1-Leu-γ2-Leu (SEQ ID NO: 14);
(7) α1-Leu-β2-Leu-Arg-Leu (SEQ ID NO: 15); and
(8) α2-Leu-β1-Leu-Arg-Leu (SEQ ID NO: 16);

wherein, in formulae (5) to (8), α1 represents Asp, Asn, Glu, Gln, Thr, or Ser; α2 represents Asn, Glu, Gln, Thr, or Ser; β1 represents Asp, Gln, Asn, Arg, Glu, Thr, Ser, or His; β2 represents Asn, Arg, Thr, Ser, or His; γ1 represents Arg, Gln, Asn, Thr, Ser, His, Lys, or Asp; and γ2 represents Gln, Asn, Thr, Ser, His, Lys, or Asp.

3. A method for producing a rice plant in which the seeds of said rice plant exhibit an increase in weight, an increase in amount of fat and oil, or an increase in fat and oil content, said method comprising the step of expressing a chimeric protein in a rice plant, said chimeric protein comprising a transcription factor fused to a repressor domain sequence that converts said transcription factor into a transcription repressor, wherein said transcription factor is selected from the group consisting of (a) and (b):

(a) a protein comprising the amino acid sequence of SEQ ID NO: 4; and (b) a protein comprising the amino acid sequence of SEQ ID NO: 4 but in which 1-20 amino acids have been deleted, substituted, added or inserted, and wherein the seeds of said rice plant exhibit an increase in weight, an increase in amount of fat and oil, or an increase in fat and oil content, in comparison to a wild-type rice plant not expressing said chimeric protein.

4. The method for producing a plant according to claim 3, wherein the repressor domain sequence comprises an amino acid sequence selected from the group consisting of (1) to (8):

(1) X1-Leu-Asp-Leu-X2-Leu-X3 (SEQ ID NO: 9 with deletion of 0-10 residues from the N-terminus)
wherein X1 represents 0 to 10 amino acid residues; X2 represents Asn or Glu; and X3 represents at least 6 amino acid residues;

(2) Y1-Phe-Asp-Leu-Asn-Y2-Y3 (SEQ ID NO: 10 with deletion of 0-10 residues from the N-terminus)
wherein Y1 represents 0 to 10 amino acid residues; Y2 represents Phe or Ile; and Y3 represents at least 6 amino acid residues;

(3) Z1-Asp-Leu-Z2-Leu-Arg-Leu-Z3 (SEQ ID NO: 11 with deletion of 0-10 residues from the C-terminus and deletion of 0-2 residues from the N-terminus)
wherein Z1 represents Leu, Asp-Leu, or Leu-Asp-Leu; Z2 represents Glu, Gln, or Asp; and Z3 represents 0 to 10 amino acid residues;

(4) Asp-Leu-Z4-Leu-Arg-Leu (SEQ ID NO: 12) wherein Z4 represents Glu, Gln, or Asp;

(5) α1-Leu-β1-Leu-γ1-Leu (SEQ ID NO: 13);
(6) α1-Leu-β1-Leu-γ2-Leu (SEQ ID NO: 14);
(7) α1-Leu-β2-Leu-Arg-Leu (SEQ ID NO: 15); and
(8) α2-Leu-β1-Leu-Arg-Leu (SEQ ID NO: 16)

wherein, in formulae (5) to (8), a1 represents Asp, Asn, Glu, Gln, Thr, or Ser; α2 represents Asn, Glu, Gln, Thr, or Ser; β1 represents Asp, Gln, Asn, Arg, Glu, Thr, Ser, or His; β2 represents Asn, Arg, Thr, Ser, or His; γ1 represents Arg, Gln, Asn, Thr, Ser, His, Lys, or Asp; and γ2 represents Gln, Asn, Thr, Ser, His, Lys, or Asp.

5. A method for isolating fat and oil from a rice plant, comprising separating and recovering fat and oil from the seeds of the plant which expresses a chimeric protein, wherein said chimeric protein comprises a transcription factor fused to a repressor domain sequence that converts said transcription factor into a transcription repressor, wherein said transcription factor is selected from the group consisting of (a)-(b):

(a) a protein comprising the amino acid sequence of SEQ ID NO: 4; and (b) a protein comprising the amino acid sequence of SEQ ID NO: 4 but in which 1-20 amino acids have been deleted, substituted, added or inserted, and wherein the seeds of said plant exhibit an increase in weight, an increase in amount of fat and oil, or an increase in fat and oil content, in comparison to a wild-type plant not expressing said chimeric protein.

* * * * *